US012490938B2

(12) United States Patent
Lee et al.

(10) Patent No.: US 12,490,938 B2
(45) Date of Patent: Dec. 9, 2025

(54) SMART MATTRESS SYSTEM AND METHODS FOR PATIENT MONITORING AND REPOSITIONING

(71) Applicants: THE BRIGHAM AND WOMEN'S HOSPITAL, INC., Boston, MA (US); Andres Rodriguez, Medford, MA (US)

(72) Inventors: Jong Woo Lee, Newton, MA (US); Andres Rodriguez, Medford, MA (US)

(73) Assignees: The Brigham and Women's Hospital, Inc., Boston, MA (US); Andres Rodriguez, Medford, MA (US)

( * ) Notice: Subject to any disclaimer, the term of this patent is extended or adjusted under 35 U.S.C. 154(b) by 916 days.

(21) Appl. No.: 17/638,620

(22) PCT Filed: Aug. 27, 2020

(86) PCT No.: PCT/US2020/048298

§ 371 (c)(1),
(2) Date: Feb. 25, 2022

(87) PCT Pub. No.: WO2021/041747

PCT Pub. Date: Mar. 4, 2021

(65) Prior Publication Data

US 2022/0330892 A1 Oct. 20, 2022

Related U.S. Application Data

(60) Provisional application No. 62/893,236, filed on Aug. 29, 2019.

(51) Int. Cl.

| | |
|---|---|
| ***A61B 5/00*** | (2006.01) |
| ***A61B 5/11*** | (2006.01) |

(Continued)

(52) U.S. Cl.
CPC .......... *A61B 5/6892* (2013.01); *A61B 5/1114* (2013.01); *A61B 5/4094* (2013.01);
(Continued)

(58) Field of Classification Search
CPC ................ A47C 27/10; A61G 7/05769; A61G 7/05776; A61G 7/001; A61B 5/6892
See application file for complete search history.

(56) References Cited

U.S. PATENT DOCUMENTS 2,434,641 A * 1/1948 Burns ................ A61G 7/05769 267/117
3,263,247 A * 8/1966 Knittel .................. A47C 27/06 297/DIG. 8

(Continued)

FOREIGN PATENT DOCUMENTS

CN 107981612 A 5/2018
CN 108125455 A 6/2018

(Continued)

OTHER PUBLICATIONS

International Search Report and Written Opinion of International Application No. PCT/US2020/048298, mailed Jan. 14, 2021, 12 pages.

*Primary Examiner* — Eric J Kurilla
(74) *Attorney, Agent, or Firm* — QUARLES & BRADY LLP

(57) ABSTRACT

Systems and methods for patient monitoring and repositioning are provided. The system includes a mattress with a cell array and a base board array to receive the cell array. The cell array includes a plurality of individually height-adjustable cells each having sensor surface configured to sense at least one biomarker of the patient while lying on the mattress. The system also includes a main unit in communication with each cell of the cell array through the base board array. The main unit is configured to receive data from each of the cells, (Continued)

including measurements of the at least one biomarker, and independently control a height of each of the cells.

19 Claims, 25 Drawing Sheets

(51) Int. Cl.
*A61G 7/012* (2006.01)
*A61G 7/018* (2006.01)

(52) U.S. Cl.
CPC ............ *A61B 5/4836* (2013.01); *A61G 7/012* (2013.01); *A61G 7/018* (2013.01); *A61B 2562/0219* (2013.01); *A61B 2562/029* (2013.01); *A61G 2203/34* (2013.01); *A61G 2203/46* (2013.01)

(56) References Cited

U.S. PATENT DOCUMENTS 3,919,730 A * 11/1975 Regan ................ A61G 7/05776 601/111
4,542,547 A * 9/1985 Sato ..................... A47C 27/082 5/713
4,799,276 A * 1/1989 Kadish ................. A61G 7/0573 5/613
4,969,684 A * 11/1990 Zarotti ................. A47C 27/082 297/284.3
5,625,914 A * 5/1997 Schwab ............... A47C 23/002 5/652
6,092,249 A * 7/2000 Kamen .................. A47C 27/10 297/284.3
6,687,937 B2 2/2004 Harker
7,069,610 B1 * 7/2006 Chai .................... G01G 19/445 177/144
7,251,845 B2 8/2007 Schaller et al.
7,434,283 B2 10/2008 Wilkinson et al.
7,513,003 B2 * 4/2009 Mossbeck ............ A47C 23/047 5/733
8,672,842 B2 3/2014 Kenalty et al.
8,752,222 B2 * 6/2014 Papaioannou ..... A61G 7/05769 5/722
9,591,995 B2 * 3/2017 Blumberg .............. A47C 17/62
9,909,772 B2 3/2018 Bazar et al.
10,292,881 B2 5/2019 Ribble et al.
10,772,446 B2 * 9/2020 Huang .................. A61B 5/1116
2006/0075559 A1 4/2006 Skinner et al.
2006/0085919 A1 4/2006 Kramer et al.
2007/0006388 A1 * 1/2007 Townsend .............. A61G 7/001 5/715
2008/0034501 A1 * 2/2008 Hyde ................. A61G 7/05707 5/613
2010/0139003 A1 * 6/2010 Moutafis .............. A47C 27/081 5/655.3
2013/0061396 A1 3/2013 Lafleche et al.
2013/0174345 A1 * 7/2013 Leu ........................ A47C 21/00 600/595
2015/0136146 A1 5/2015 Hood et al.
2017/0027792 A1 2/2017 Lafleche et al.
2017/0128297 A1 5/2017 Cernasov et al.
2017/0224565 A1 8/2017 Lachenbruch et al.
2019/0223612 A1 7/2019 Watteresson et al.

FOREIGN PATENT DOCUMENTS

CN 110292277 A * 10/2019 ........... A47C 21/048
CN 110507496 A * 11/2019 ........... A61G 5/1045
GB 2362567 A * 11/2011 ........... A47C 27/081

* cited by examiner

NODE TOUCH POINT SAMPLING

PRESSURE MAP

SMART MATTRESS SYSTEM AND METHODS FOR PATIENT MONITORING AND REPOSITIONING

CROSS-REFERENCE TO RELATED APPLICATIONS

This application is based on, claims priority to, and incorporates herein by reference in its entirety, U.S. Provisional Patent Application Ser. No. 62/893,236, filed on Aug. 29, 2019.

STATEMENT REGARDING FEDERALLY FUNDED RESEARCH

N/A

BACKGROUND

Sudden Unexpected Death in Epilepsy (SUDEP) is the leading cause of death in epilepsy children and otherwise healthy adult epilepsy patients, affecting about 1.2 per 1000 patients, and with a cumulative lifetime risk of approximately 8%. Furthermore, the risk of SUDEP is higher with respect to nocturnal seizures, as about 70% of SUDEP occurs during sleep. This higher risk may be due to greater cardiorespiratory instability during sleep, postictal airway obstruction from bedding or prone positioning, and increased likelihood of being alone. For example, though the exact mechanisms of SUDEP are still not completely understood, after a convulsive seizure, there is depressed level of consciousness and impaired arousal. Additionally, peri-ictal respiratory dysfunction is typically severe, with a decrease in oxygen saturation. This leads to a combination of poor respiratory mechanics, arousal failure, and decreased respiratory drive, leading to apnea (cessation of respiration) within approximately three minutes. Evidence therefore suggests that there is less than a three-minute window for intervention before terminal apnea.

A noted major risk factor contributing to SUDEP is being in a prone position at the end of a generalized convulsive seizure, as nearly 90% of patients in sleep-time SUDEP cases are found in the prone position. Furthermore, every patient who has succumbed to SUDEP while being monitored by video EEG died in the prone position. Thus, by avoiding the prone position after a generalized tonic-clonic seizure (GTCS) at night, the risk of night-time SUDEP can likely be greatly reduced.

Accordingly, simple interventions such as turning and stimulating the patient may substantially decrease SUDEP risk. For example, patients in an epilepsy monitoring unit rarely die in the hospital; they are revived without any advanced or intensive resuscitation measures and are always turned away from the prone position. Furthermore, at home, merely having supervision or a bed partner can decrease the risk of SUDEP (e.g., by the partner recognizing the seizure and stimulating the patient). Such in-person supervision, however, is not always feasible.

Furthermore, current intervention options are generally insufficient. For example, one current solution for nocturnal supervision of patients with frequent generalized tonic-clonic and nocturnal seizures includes using remote listening devices. Although a remote listening device may present an opportunity for intervention in the case of a seizure, it may not be available with enough rapidity to consistently deliver treatment within the critical, three-minute window. Moreover, current devices do not have the ability to intervene and prevent SUDEP on their own. Additionally, daily use of such devices is likely challenging, given the need to remember to wear the device, charge the battery, and establish a reliable network for alerts. As another potential solution, anti-asphyxia pillows and mattress toppers have been developed to reduce airflow resistance and prevent suffocation (e.g., while in the prone position), but carbon dioxide retention of such products is still considered potentially life-threatening.

In light of the above, it may be desirable to provide systems and methods to solve the above unmet needs for patients with epilepsy, including autonomously performing critical interventions associated with nocturnal supervision, such as repositioning and stimulating a patient after a convulsive seizure.

SUMMARY

The systems and methods of the present disclosure overcome the above and other drawbacks by providing systems and methods for patient monitoring and autonomous repositioning through a smart mattress including an array of height-adjustable cells that can be individually controlled.

In accordance with one aspect of the disclosure, a system for patient monitoring and repositioning is provided. The system includes a mattress with a cell array and a base board array to receive the cell array. The cell array includes a plurality of individually height-adjustable cells each having a sensor surface configured to sense at least one biomarker of the patient while lying on the mattress. The system also includes a main unit in communication with each cell of the cell array through the base board array. The main unit is configured to receive data from each of the cells, including measurements of the at least one biomarker, and independently control a height of each of the cells.

In accordance with another aspect of the disclosure, a smart cell for use in a smart cell array that forms a smart mattress is provided. The smart cell includes a cushion layer, a spring layer, and a platform layer. The cushion layer includes a cushion cover over a sensor module, and the sensor module is configured to sense at least one biomarker associated with a user lying on the cushion layer. The spring layer includes an expandable spring configured to adjust an overall height of the smart cell. The platform layer is configured to support the spring layer and the cushion layer and house a terminal board. The terminal board is configured to control the expandable spring to adjust the overall height of the smart cell.

In accordance with yet another aspect of the disclosure, a method for monitoring and repositioning a patient using a smart mattress system is provided. The method includes scanning the patient on the smart mattress system using a smart cell array including individual cells each having an independent sensing surface, and identifying a position of the patient on the smart mattress based on the scanning. The method also includes determining when the patient's position is a prone position, and automatically adjusting heights of one or more of the individual cells to reposition the patient out of the prone position.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The disclosure provides systems and methods for monitoring and managing patients while in bed. In particular, the disclosure provides a patient monitoring system with a smart mattress configured to autonomously monitor, reposition, and/or stimulate a patient and associated operating methods. For example, the smart mattress includes a cellular construction, comprised of an array of individual cells, that allows for the creation of a kinetic sleeping device that is robotically controlled, able to deliver assistance to patients in bed to reposition them while asleep without human intervention. The cells also are sensing nodes that enable the possibility to scan, monitor, and track the health of specific parts of the body facing the cell. In one application, the systems and methods monitor and manage patient seizures during sleep, for example, to decrease the risk of Sudden Unexpected Death in Epilepsy (SUDEP). In other applications, the system and methods may be used for in-bed health monitoring, for safe sleep practices, as bed mobility aids, for in-bed therapies, for positional breathing therapies, and/or other monitoring, therapies, or treatments.

Figure 1:
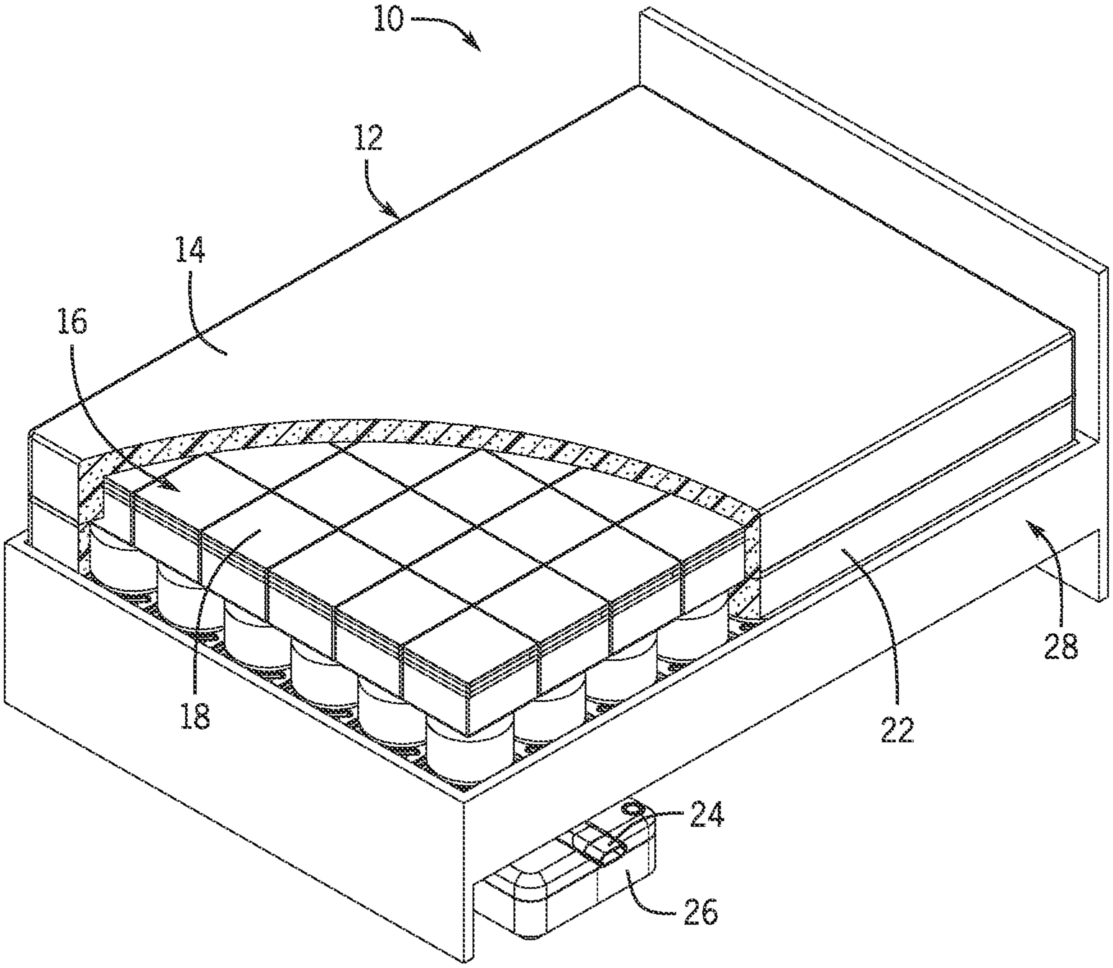
FIG. 1 is a perspective view of a patient management system in accordance with the present disclosure.
Figure 2:
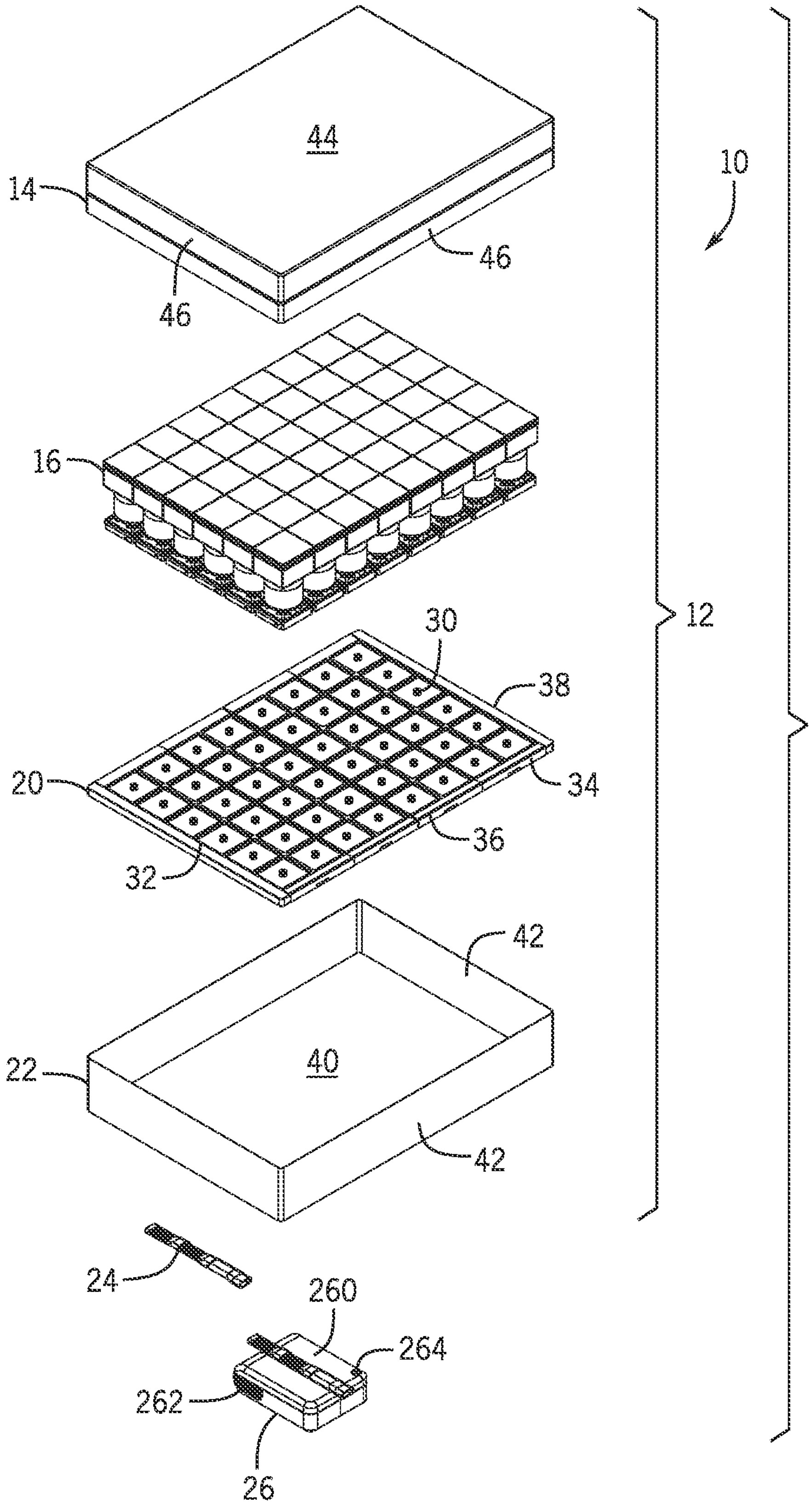
FIG. 2 is an exploded perspective view of the patient management system of FIG. 1.

FIG. 1 illustrates a patient management system 10 in accordance with the present disclosure. Generally, the system 10 can be configured to continuously monitor a user lying on a mattress 12 through an array of sensors, autonomously reposition the patient to an optimal position (e.g., by preventing a prone position and moving the patient to a recovery position), and stimulate the patient (e.g., after a seizure). As shown in FIGS. 1 and 2, the system 10 can generally include the mattress 12 with a mattress pad 14, a smart cell array 16 of individual cells 18, a base board array 20, and a mattress skirt 22, a main line 24, a main unit 26, and a frame 28.

With respect to the mattress 12, generally, the mattress pad 14 and the mattress skirt 22 can fit together to enclose the base board array 20 and the smart cell array 16, for example, to at least partially protect those components from dust and/or liquid. As further described below, the smart cell array 16 is a modular component made of up of an array of cells 18 individually configured to sense user biomarkers and lift upward or drop downward along a z-axis. Each cell 18 of the smart cell array 16 can correspond to a respective base board 30 of the base board array 20. That is, the number of individual cells 18 in the system 10 can be equal to the number of individual base boards 30 in the system 10. Accordingly, the base board array 20 can also be a modular component made up of individual base boards 30, or smaller arrays of base boards 30 (such as a lower base board array 32, an upper base board array 34, and one or more intermediate base board arrays 36), encircled by a frame 38, as shown in FIG. 2. The frame 38 may act as a conduit for electrical and/or pneumatic connections between the main line 24 and individual base boards 30 (e.g., for air distribution, power supply, and/or data exchange, as further described below).

Accordingly, due to the modularity of the smart cell array 16 and the base board array 20, the arrays 16, 20 can be formed in any size and shape for a particular application. For example, the system 10 can include arrays 16, 20 with individual cells 18 and base boards 30 arranged to match dimensions of standard mattresses, such as crib, twin, full, queen, king, California king, or other custom sizes and shapes. Furthermore, mattresses 12 can be resized by removing or adding cells 18 and base boards 30 to the arrays 16, 20, and individual components may be replaced when needed, extending the life of the system 10. For example, the mattress 12 may be able to "grow" as the user grows. The modular assembly can also permit simple transfer of components compared to a standard mattress, for example, by shipping individual cells 18 and assembling the system 10 on-site (as further described below). In the same manner, the modular assembly can permit easier recycling and disposal.

In some applications, the mattress pad 14, the mattress skirt 22, and the frame 28 can be sized to correspond to standard bed or mattress sizes, or custom sizes, and can substantially match the dimensions of the smart cell array 16 and the base board array 20. The frame 28 can support the mattress 12 while also permitting space for connections between the mattress 12 and the main unit 26 via the main line 24 (e.g., between a source connector of the base board frame 38 and the main line 24). The mattress skirt 22 can sit within the frame 28 and include a base portion 40 and side portions 42 extending upward from edges of the base portion 40, as shown in FIG. 2. Alternatively, in some applications, the mattress pad 14 may instead comprise a separate flat pad and a covering (not shown) extending over and around the sides of the flat pad, thus forming the base portion 44 and the side portions 46. Furthermore, the mattress pad 14 can include a base portion 44 and side portions 46 extending downward from edges of the base portion 44 so that, when assembled, the side portions 42, 46 of the mattress skirt 22 and the mattress pad 14 are adjacent to each other and, in some cases, engage each other, enclosing the arrays 16, 20.

Additionally, as noted above, the cells 18 of the smart cell array 16 can individually be moved up and down (e.g., along a z-axis). As a result, at least the base portion 44 of the mattress pad 14 can be sufficiently flexible to be raised or lowered in response to movement of individual cells 18 beneath it. The base portion 44 of the mattress pad 14 can also provide sufficient cushion to the user. Though not shown, in some applications, the mattress 12 can also include additional structural features, such as additional frame components around the mattress 12, to provide more structure to the mattress pad 14 and the mattress skirt 12 and to help protect the cell array 16 from lateral impacts, for example.

Figure 9:
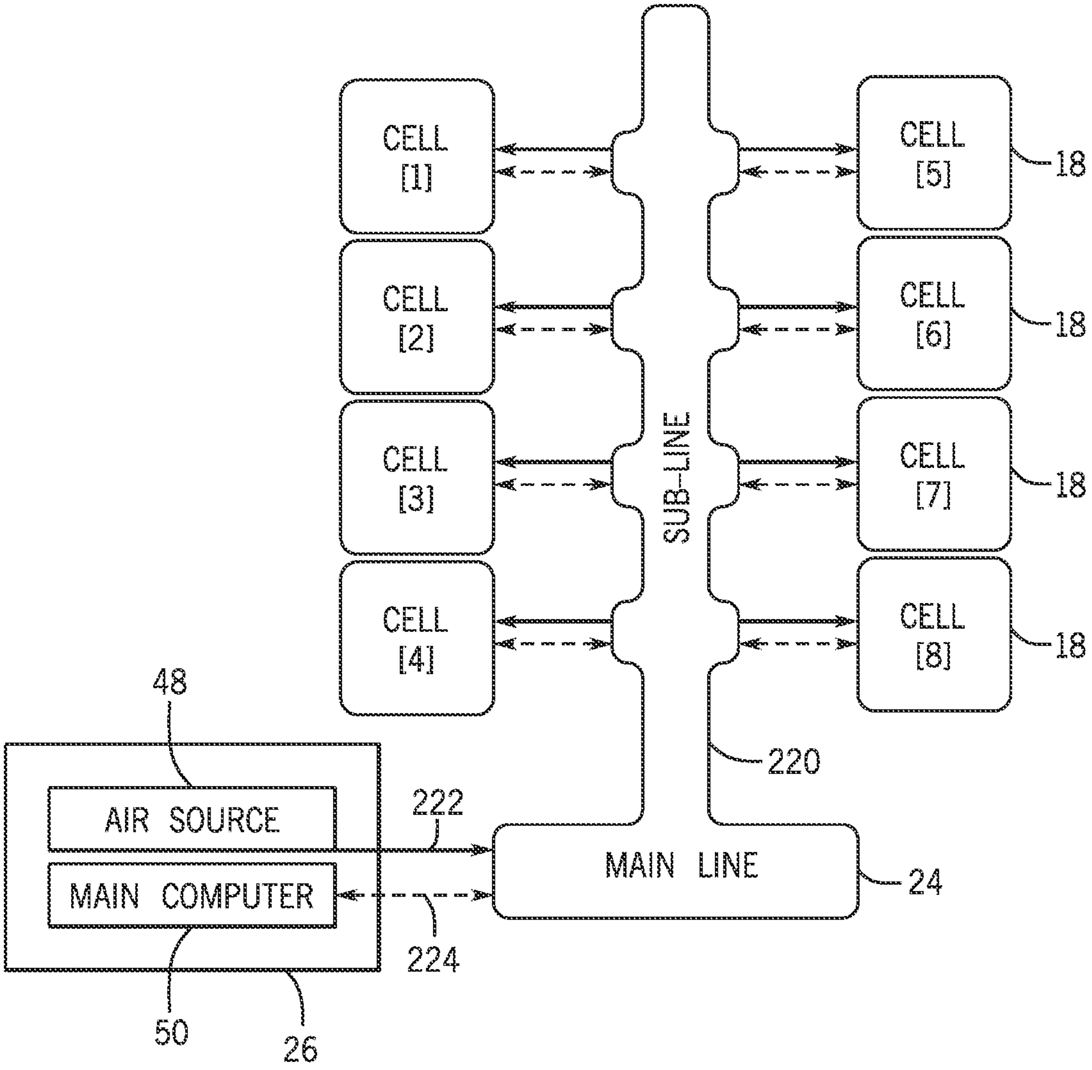
FIG. 9 is a schematic view of an architecture of system connections of the patient management system of FIG. 1

In order to monitor and/or reposition a user lying on the mattress pad 14, as further described below, each cell 18 in the smart cell array 16 can be electrically and pneumatically connected to the main unit 26 via the base board array 20 and the main line 24. More specifically, the main unit 26 can include an air source 48 and a main computer 50 in communication with each cell 18 (for example, as shown in FIG. 9). As shown in FIGS. 1 and 2, the main unit 26 can be stored underneath the frame 28, although other locations may be contemplated in some applications. Thus, the main unit 26 and the main line 24 can be stored underneath the frame 28, while the mattress pad 14, the smart cell array 16, the base board array 20, and the mattress skirt 22 can be stored on top of and supported by the frame 28.

Figure 3A:
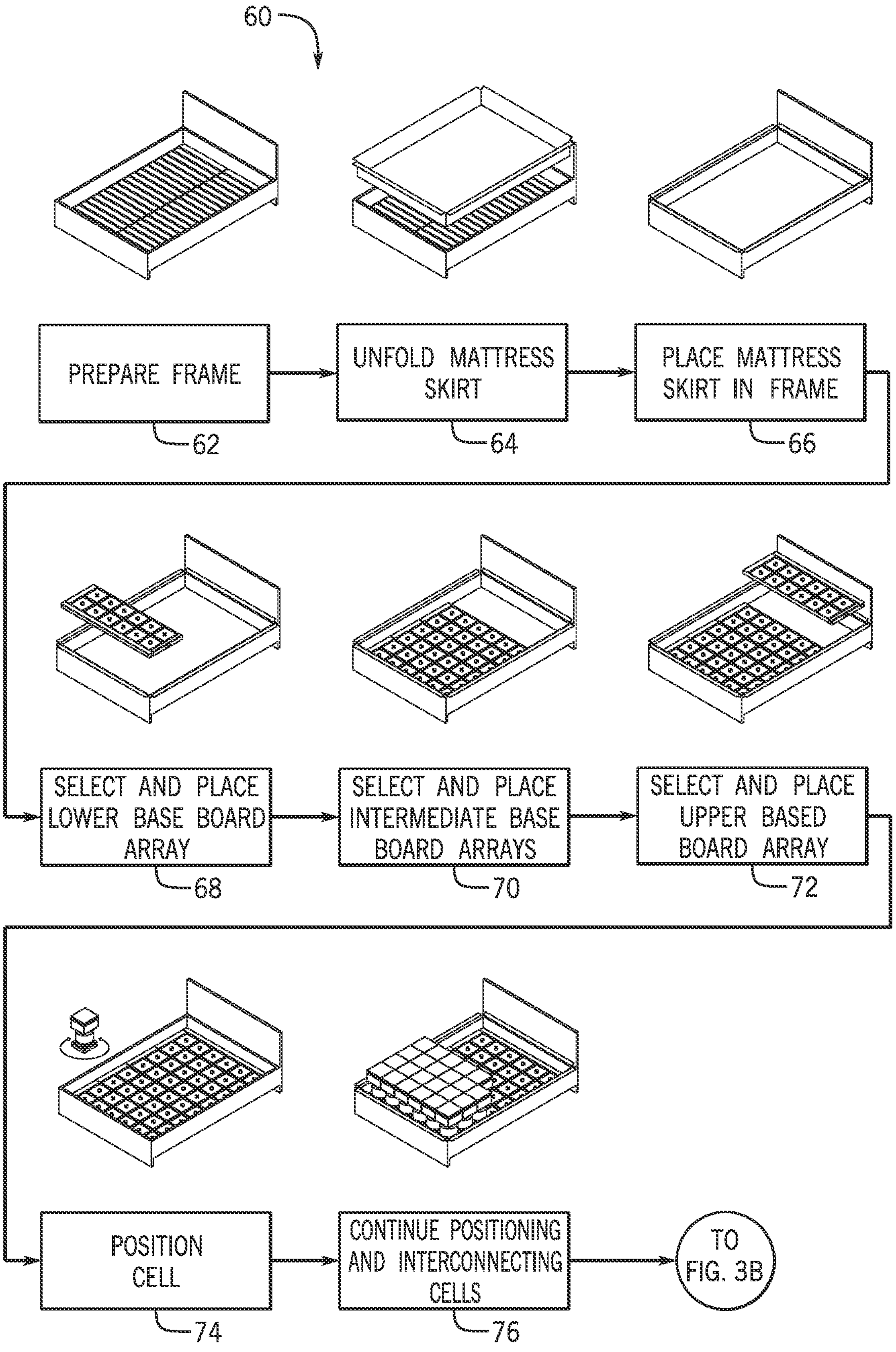
FIGS. 3A and 3B illustrate a method for assembling the patient management system of FIG. 1.
Figure 3B:
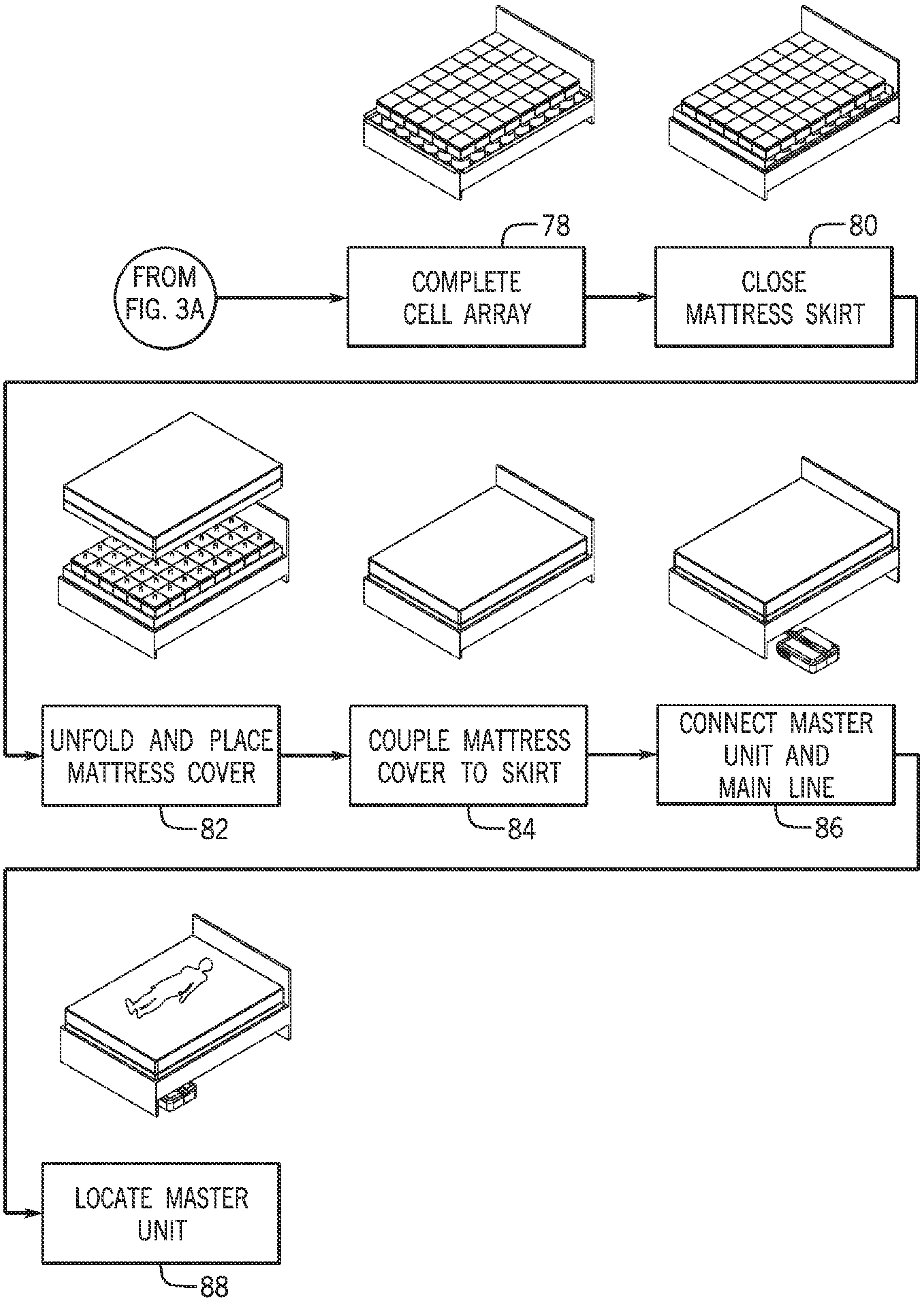

More specifically, FIGS. 3A-3B illustrate a method 60 for assembling the system 10 according to some embodiments. First, at step 62, the frame is prepared. At step 64, the mattress skirt 22 is unfolded, that is, the side portions 46 of the mattress skirt 22 are at least partially folded outward away from each other. At step 66, the unfolded mattress skirt 22 is placed in the frame 28. At step 68, a lower base board array 32 is selected and placed on the base portion 40 of the mattress skirt 22. At step 70, one or more intermediate base board arrays 36 are selected, placed on the base portion 40 of the mattress skirt 22 adjacent the lower base board array 32, and connected to the lower base board array 32. At step 72, an upper base board array 34 is selected, placed on the base portion 40 of the mattress skirt 22 adjacent the intermediate base board array 36, and connected to the intermediate base board array 36. Accordingly, in the embodiment illustrated in FIG. 3A and further described below, the base board array 20 comprises multiple smaller base board arrays 32, 34, 36 of individual base boards 30. However, in other embodiments, steps 68-72 can include selecting, positioning, and connecting individual base boards 30 to form the base board array 20.

Once the base board array 20 is completed, at step 74, a first cell 18 is positioned and placed over a respective base board 30. Step 76 is then repeated until each base board in the base board array 20 is covered by a respective cell 18. Thus, at step 78, the smart cell array 16 is completed. At step 80, the mattress skirt 22 is closed by folding back up the side portions toward each other. At step 82, the mattress pad 14 is unfolded and placed over the smart cell array 16. At step 85, the mattress pad 14 is coupled to the mattress skirt 22. In one example, outer edges of the side portions 42, 46 have corresponding zippers, allowing the mattress pad 14 to be zippered to the mattress skirt 22.

Once step 84 is completed, the mattress 12 is assembled. Following step 84, at step 86, the main line 24 is connected to the base board array 20 in order to connect the main unit 26 to the smart cell array 16. Once step 86 is completed, the main unit 26 is located and the system is ready for use (step 88). Generally, the main unit 26 can be located in a safe place in an organized manner to prevent the risk of disconnecting the main line 24 from the main unit 26 (such as adjacent the mattress 12 without leaving any space between them). More specifically, depending on the type or size of mattress, a user can locate the master unit 26 underneath the mattress 12 (as described above), next to the mattress 12, attached to one the baseboard array, or at another suitable location.

Figure 4:
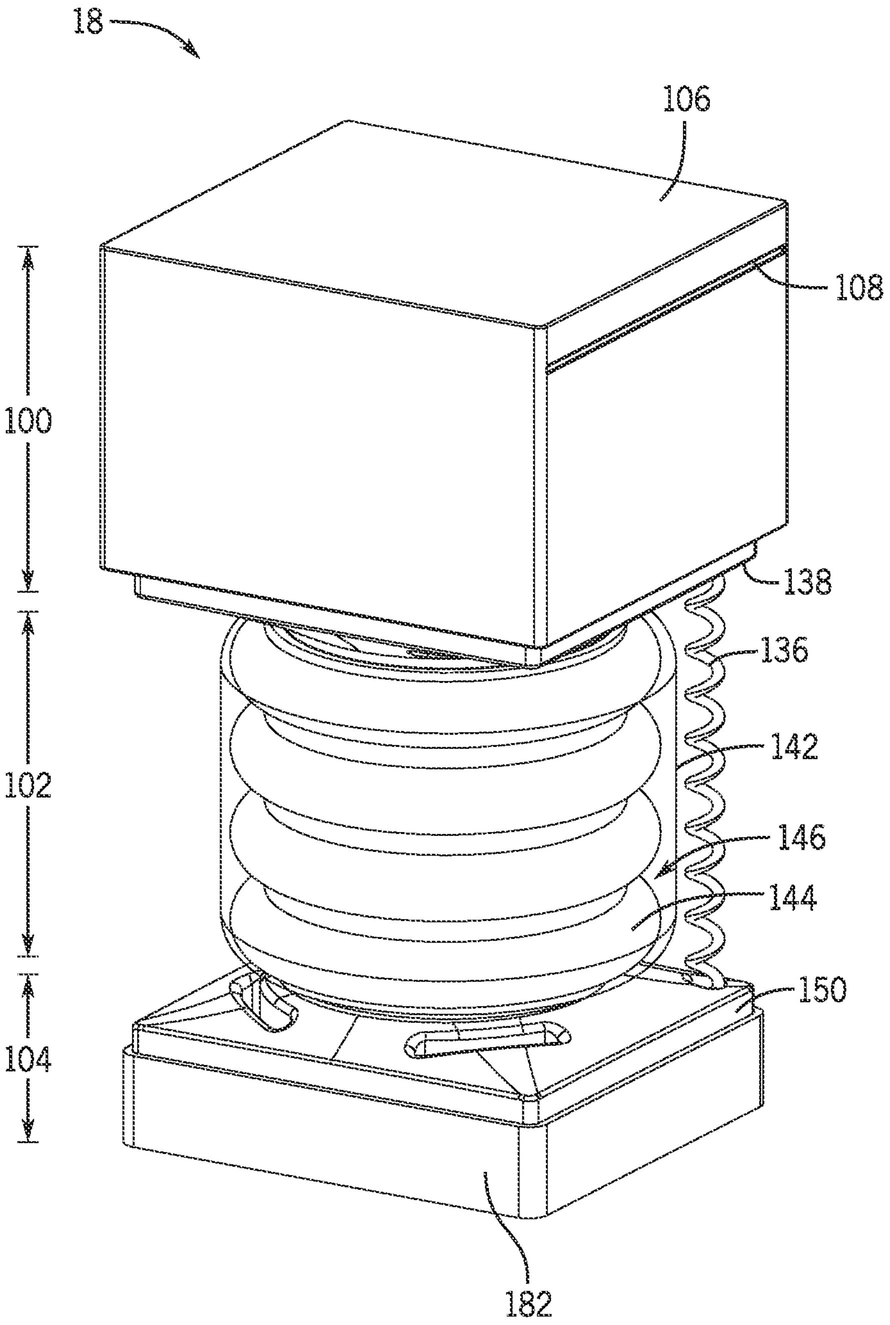
FIG. 4 is a perspective view of a smart cell for use with the patient management system of FIG. 1.
Figure 5:
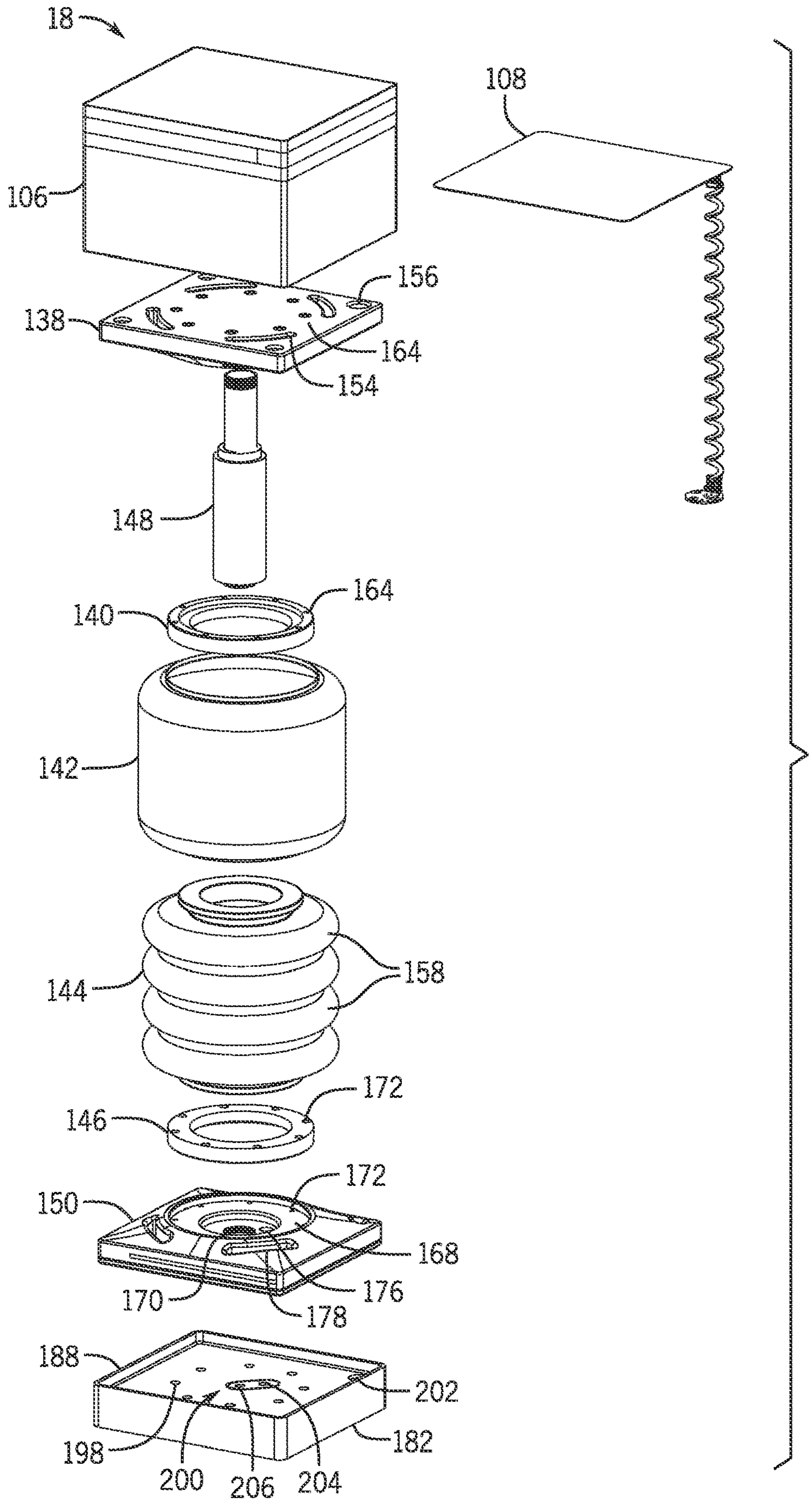
FIG. 5 is an exploded perspective view of the smart cell of FIG. 4.
Figure 6:
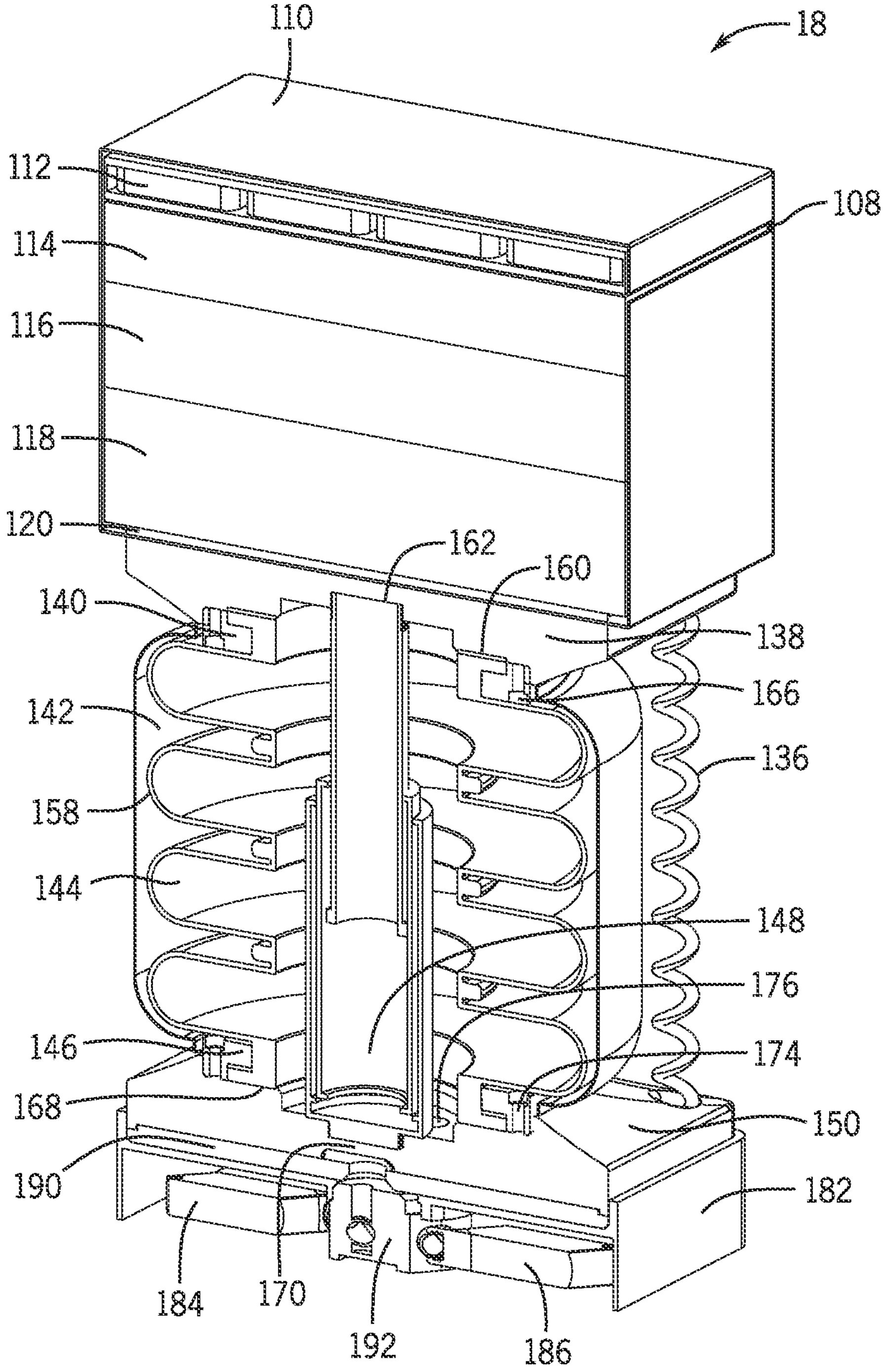
FIG. 6 is a cross-sectional view of the smart cell of FIG. 4.

With further reference now to components of the system, FIGS. 4-6 illustrate an individual smart cell 18. As shown in FIGS. 4-6, each smart cell 18 can include a pad portion 100, a spring portion 102, and a platform portion 104. Generally, the pad portion 100 can soften contact with the structure of the cell 18 and house an array of sensors. The spring portion 102 can expand in the Z-axis, moving the cell 18 upward or downward to help adjust a user while the user lays on the mattress 12. The platform portion 104 can secure the cell 18 to the base board 30, house electronics necessary to communicate with the main unit 26, and control air flow to the spring portion 102.

More specifically, the pad portion 100 can include a cushion 106 to form a comfortable surface as cells 18 interconnect, and a sensor module 108 configured to sense biomarkers associated with a user lying on the cushion 106. The cushion 106 can include a cushion cover 110, a sensor layer 112, one or more foam density layers (such as a low density layer 114, a medium density layer 116, a high density layer 118), and a pad holder 120. The cushion cover 110 and the pad holder 120 can enclose the sensor and foam layers 112-118 as well as the sensor module 108. For example, the pad holder 120 can be substantially cuboid in shape with an open top to receive the foam density layers 114-118, the sensor module 108, and the sensor layer 112, and the cushion cover 110 can sit atop the sensor layer 112 to form a closed cube. While three foam layers 114-118 are illustrated in FIG. 6, in some applications, fewer, additional, or alternative layers of materials or components can be included in the cushion 106, such as other types of foam density layers, inflatable pads, microstructure rubber pads, and/or gel bag pads to customize the cushion based on patient needs. Additionally, while the pad portion 100 is illustrated and described as cuboidal in shape, in some applications, the pad portion 100 may take on other shapes such as, but not limited to, cylindrical.

Figure 7:
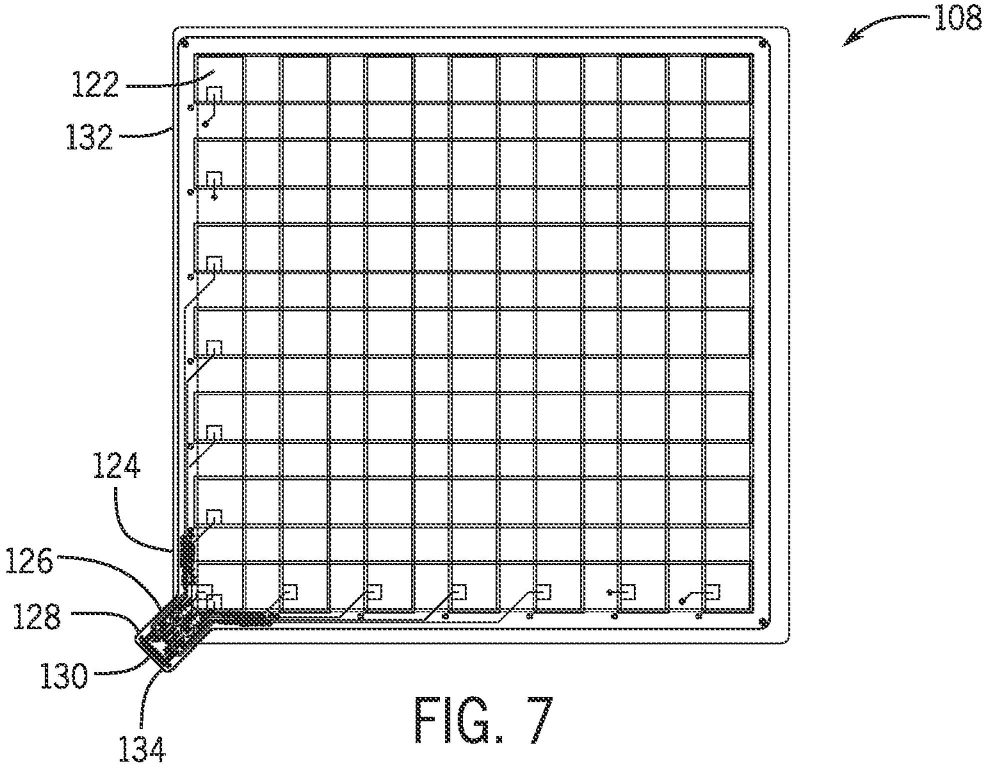
FIG. 7 is a top view of a sensor module of the smart cell of FIG. 4

The sensor module 108 can be a substantially thin sensing system configured to sense various biometric variables of a user while lying on the cell 18. In some applications, the sensor module 108 is flexible, soft, and substantially thin, such as about 1 millimeter thick, and can be slid into the sensor layer. In some embodiments, the sensor module 108 can be slid into the cushion 106, for example, into the sensor layer 112 (e.g., a pocket inside the cushion 106). By way of example, as shown in FIG. 7, the sensor module 108 can be a multi-sensor sheet integrating one or more arrays of sensors including, but not limited to, one or more pressure sensors 122, one or more accelerometers 124, one or more temperature sensors 126, one or more sound frequency sensors 128, and/or one or more humidity sensors 130. For example, each sensor module 108 can include a sensor pocket 132, an array of pressure sensors 122 across a portion of or an entire area of the sensor pocket 132, and a single accelerometer 124, temperature sensor 126, frequency sensor 128, and humidify sensor 130 associated with the sensor pocket 132. Furthermore, the sensors 122-130 can be connected to a multi-sensor terminal 134. The multi-sensor terminal 132 can be electrically coupled to a sensor cable 136 (shown in FIGS. 4 and 5, for example, routed through a channel, not shown, in the cushion 106), which can be further coupled to the platform portion 104 for electrical connection to the main line 24, as described below.

The pad portion 100, therefore, serves to provide a comfortable surface for the user as well as a sensing surface for monitoring the user's biometric information. The pad portion 100 further is moved up and down, via the spring portion 102, in order to adjust the user's position on the mattress 12. More specifically, the pad portion 100 sits atop the spring portion 102 and is movable up and down along a z-axis. To accomplish this movement, the spring portion 102 can incorporate a pneumatically operated, expandable spring. More specifically, as shown in FIGS. 5 and 6, the spring portion 102 can include a top plate 138, an upper ring air seal 140, a spring cover 142, the expandable spring 144, a lower ring air seal 146, a telescopic bar 148, and an air platform 150.

Generally, the spring 144 and the telescopic bar 148 can be enclosed inside a spring cavity 152 formed by the top plate 138, the spring cover 142, and the air platform 150. The spring cavity 152 can further be substantially sealed by the upper ring air seal 140 positioned between the top plate 138 and the spring cover 142, and by the lower ring air seal 146 positioned between the spring cover 142 and the air platform 150. That is, the upper ring air seal 140 can seal the spring 144 within the spring cavity 152 to substantially prevent air leakage and interfaces with the top plate 138 and the spring 144, as well as the spring cover 142. Similarly, the lower ring air seal 146 can seal the spring 144 within the spring cavity 152 to substantially prevent air leakage and interfaces with the air platform 150 and the spring 144, as well as the spring cover 142.

For example, as shown in FIG. 6, the top plate 138 can be coupled to upper ends of the telescopic bar 148, the spring 144, and the spring cover 142 and can face, support, and hold the pad portion 100. More specifically, in some applications, the top plate 138 can include a ring seat 160 to receive the upper ring air seal 140, the spring 144, and the spring cover 142, and a bar seat 162 to receive the telescopic bar 148. The ring seat 160 and the upper ring air seal 140 can include corresponding apertures 164 to fasten the components 138, 140 together (via fasteners 166) and, as a result, maintain the spring 144 and the spring cover 142 against the top plate 138 to seal the spring 144. The top plate 138 can also include air channels 154, as shown in FIG. 5, located outside of the ring seat 160, to distribute air through the cushion 106 for ventilation, for example, to improve airflow and minimize temperature increases along the mattress surface. The top plate 138 can further include a cable port 156 sized to permit the sensor cable 136 to pass through. In some applications, the top plate 138 can comprise stainless steel.

The inflatable spring 144 can act as the main component generating mechanical power inside the cell 18, and inflates and deflates to adjust its height, while keeping its stiffness pushing up or down the top layers of the mattress 12. More specifically, the inflatable spring 144 can include air or another gas and can be configured to expand and contract along the z-axis, forcing the pad portion 100 upward (for example, in a positive Z direction) to lift a user at the individual cell 18, or lower the cell 18 down to a nominal height (or below a nominal height, for example, in a negative Z direction). The spring 144 can expand or contract by adding or venting air, respectively, thus changing an internal pressure inside the spring 144, causing individual rings 158 of the spring 144 to expand away for or contract toward each other. Thus, the spring 144 can include a specific number and size of rings 158 configured to provide an expansion distance corresponding to a desired total height change ("lift') of the cell 18. In one application, each individual cell 18 can be configured to withhold a capacity of 6000 pounds per cell 18 and achieve approximately 14 inches of lift at a rate of two inches per second. In some applications, each individual cell 18 can be configured to achieve a maximum lift height within about 5-20 seconds.

The telescopic bar 148 can be located inside the spring cavity 152 and, for example, encircled by the spring 144. The telescopic bar 148 can help keep the horizontal integrity of the cell 18 and, at the same time, act as a suspension system to soften the impact of a user lying on the cell 18 (which generally comprises a substantially rigid platform portion 104). As a result, the telescopic bars 148 of interconnected cells 18 can make the overall mattress surface feel softer and less rigid. Structurally, the telescopic bar 148 can be coupled to the top plate 138 and the air platform 150 and, thus, can expand (i.e., by telescoping components expanding away from one another) and contract (i.e., by telescoping components telescoping into one another) with the spring 144. The telescopic bar 148 can further include an internal spring and a set of vertical bearings (not shown) that can reduce friction between the components, attenuating noise and resistance when the cell 18 is raised and lowered.

The spring cover 142 can act to keep the spring 144 and telescopic bar 148 within the spring cavity 152 substantially clean, preventing accumulation of dust, humidity, and general contaminates that can accumulate around the spring rings 158. The spring cover 142 can comprise stretchable material as it must expand and contract with movement of the spring 144. For example, in one application, the spring cover 142 can comprise latex. In other applications, the spring cover 142 can comprise other stretchable materials such a neoprene, spandex, or rubber.

The air platform 150 can distribute air inside the spring 144 and can act as a base of the spring portion 102. As shown in FIG. 5, the air platform 150 can include a ring seat 168 to receive the lower ring air seal 146, the spring 144, and the spring cover 142, and a bar seat 170 to receive the telescopic bar 148. The ring seat 168 and the lower ring air seal 146 can include corresponding apertures 172 to fasten the components 150, 146 together (via fasteners 174) and, as a result, maintain the spring 144 and the spring cover 142 against the air platform 150 to seal the spring 144. The air platform 150 can also include one or more ports 176 positioned inside of the ring seat 168 and configured to permit air to pass into and out of the spring 144 for expansion and contraction. The air platform 150 can further include air channels 178 positioned outside of the ring seat 168. The air channels 178 can distribute air around the spring cover 142 for surface ventilation (e.g., through the air channels 154 of the top plate 138).

The air platform 150 can further interface with the platform portion 104, which can secure the cell 18 to a base board 30 and interlink a base board port interface 180 (shown in FIG. 8) to the main line 24 for air distribution and electrical connections. For example, the platform portion 104 can include a motion terminal 182 that encloses the pneumatic and electrical system of the cell 18. More specifically, as shown in FIG. 6, the platform portion 104 can include the motion terminal 182, a spring activation valve 184, a ventilation valve 186, a terminal board 188 (shown in FIG. 10), a receiving plate 190, and a connection manifold 192.

As shown in FIGS. 5 and 6, the motion terminal 182 can include a seat 194 with raised edges 196. The receiving plate 190 can sit within the seat 194 (e.g., between the motion terminal 182 and the air platform 150), as shown in FIG. 6. Generally, the receiving plate 190 can seal fluid channels of the air platform 150 and interfaces the air platform 150 with the motion terminal 182. In some applications, the receiving plate 190 can include an airtight portion (such as a plastic part with a gasket, not shown) to frame and seal the ventilation channels 178 and/or fluid ports 200. Furthermore, in some applications, the receiving plate 190 can include indication marks (not shown) to help guide a user during assembly.

Along the seat 194, the motion terminal 182 can include fastening apertures 198, one or more fluid ports 200, and a cable port 202. The fastening apertures 198 can receive fasteners (not shown), for example, to couple the air platform 150 to the motion terminal 182. The fluid ports 200 can include a spring port 204 to supply air to the spring 144 for spring expansion and a ventilation port 206 to ventilate air from the spring 144 for spring contraction, which can interface with the connection manifold 192. The cable port 202 can permit the sensor cable 136 to pass through the motion terminal 182 and electrically connect to the terminal board 188, which may be positioned underneath the seat 194.

Figure 8:
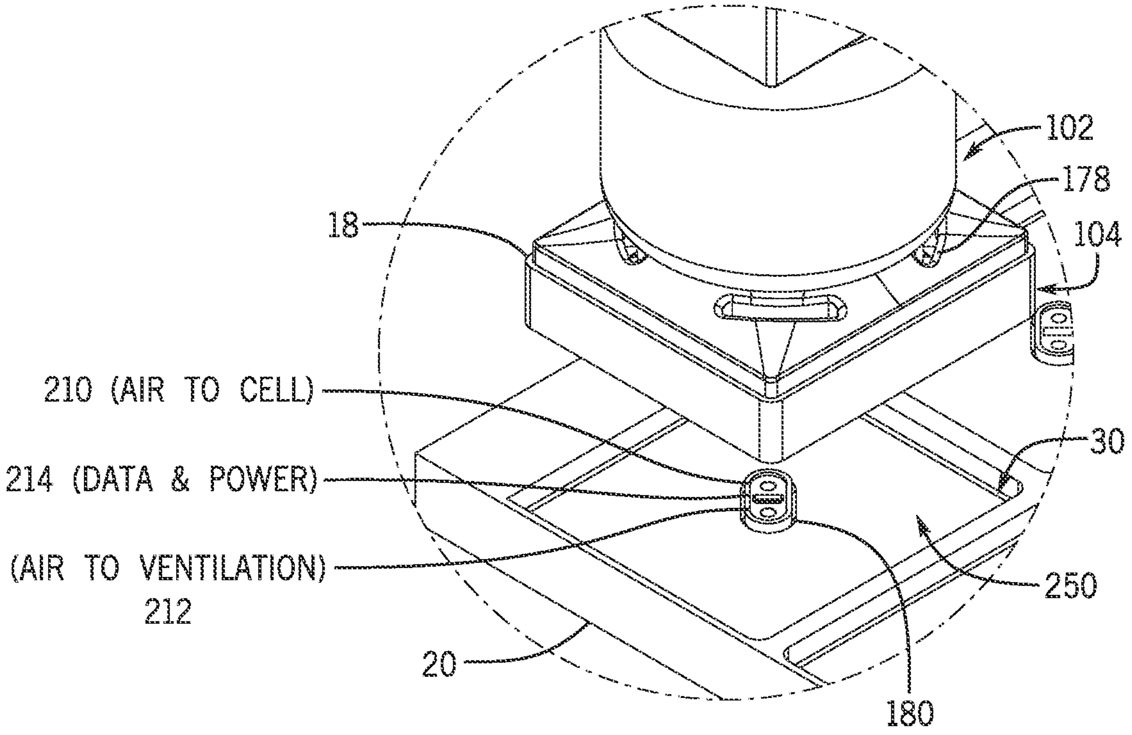
FIG. 8 is a partial perspective view of the smart cell of FIG. 4 and a base board array for use with the patient management system of FIG. 1.

In particular, underneath the seat 194, the motion terminal 182 can define a cavity to house the valves 184, 186, the connection manifold 192, and the terminal board 188. The connection manifold 192 can communicate with an interface 180 of a base board 30, as shown in FIG. 8. More specifically, the connection manifold 192 can be coupled to the base board interface 180 (e.g., via a snap fit connection) in order to physically, electrically, and pneumatically connect the cell 18 to the base board 30. For example, the connection manifold 192 can interlink the spring port 204 with a spring port 210 of the base board interface 180, which can place the spring port 204 in communication with an air source 48 of the main unit 26 via the main line 24. The connection manifold 192 can further interlink the ventilation port 206 with a ventilation port 212 of the base board interface 180, which can place the ventilation port 206 in communication with ventilation channels (such as air channels 178). The air channels 178 can then distribute air through the mattress 12 (e.g., generally from all channels 178 or through specific channels 178 to distribute or circulate air at different sections of the mattress 12). Finally, the connection manifold 192 can electrically interlink the terminal board 188 with a data/power port 214 of the base board interface 180, which can place the terminal board 188 in electrical communication with the main unit 26 via the main line 24 (and sub-lines through the base board frame 38, as further described below).

With respect to the interlinked spring ports 204, 210, the spring activation valve 184 (such as a solenoid valve) can be actuated to selectively connect or disconnect the spring ports 204, 210. For example, the spring activation valve 184 can be actuated to connect the spring port 210 of base board interface 180 to the spring port 204 of the motion terminal 182, thus providing air from the air source 48 to the spring 144 to expand the spring 144. Similarly, with respect to the interlinked ventilation ports 206, 212, the ventilation valve 186 can be actuated to selectively connect or disconnect the ventilation ports 206, 212. For example, the ventilation valve 186 can be actuated to connect the ventilation port 212 of the base board interface 180 to the ventilation port 206 of the motion terminal 182, thus venting air from the spring 144 to contract the spring 144. The valves 184, 186 can be electrically connected and controlled by the main unit 26 via the terminal board 188.

More specifically, the terminal board 188 can serve as the local controller of the cell 18, connecting the cell 18 to the main unit 26 for data communication and power. Accordingly, the valves 184, 186 and the sensor module 108 (via the sensor cable 136) can be in electrical communication with the terminal board 188. As noted above and shown in FIG. 8, the base board interface 180 can include a data/power port 214 that can be connected to the terminal board 188 when the cell 18 is installed on the base board 30 (for example, via a data transfer port (not shown) of the connection manifold 192 that can plug into the data/power port 214). The data/power port 214 of the interface 180 can further be connected to the main line 24, which is connected to the main unit 26. As a result, power and data can be communicated to the cell 18 from the main unit 26 via the main line 24, the base board frame 38, the base board interface 180, to the terminal board 188. Some example data/power ports 214 that may be used include Thunderbold, USB 3.1, USB 3.0, or other suitable ports. Additionally, while data transfer between the cells 18 and the main unit 26 is described herein via wired connections, in some applications, other data transfer technologies, such as WiFi or Bluetooth, may be utilized.

By way of example, FIG. 9 illustrates a schematic architecture of system connections. As shown in FIG. 9, the main unit 26 includes the air source 48 and the main computer 50. The main unit 26 is connected, via the main line 24, to one or more sub-lines 220 (e.g., along base board frames 38). From the sub-lines 220, the main unit 26 is further connected to each individual cell 18 (e.g., via connections from the sub-lines 220 to each base board interface 180, then to the connection manifold 192 and, in turn, to air ports 200 and the terminal board 188 of each cell 18). In some applications, each base board array 32, 34, 36 includes one sub-line 220, which then branches out to individual cells 18.

Figure 11A:
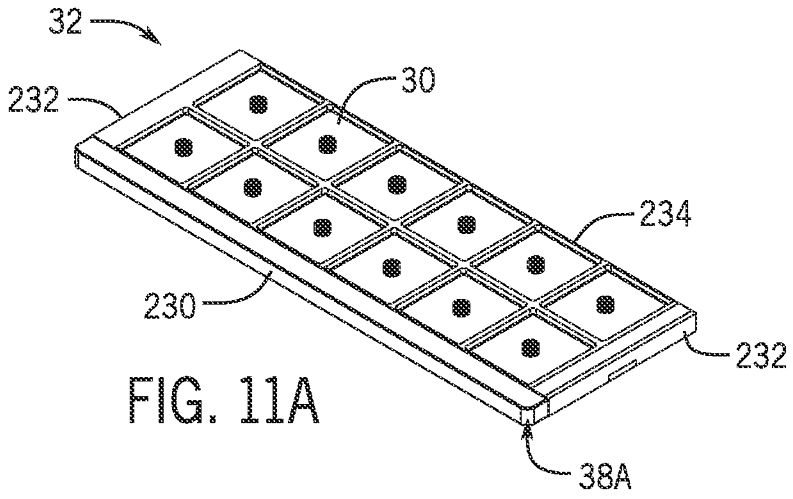
FIGS. 11A-11E are different views of base board arrays, including a lower base board array (FIG. 11A), an upper base board array (FIG. 11B), an intermediate base board array (FIG. 11C), a partially assembled base board array (FIG. 11D), and an assembled base board array (FIG. 11E).
Figure 11B:
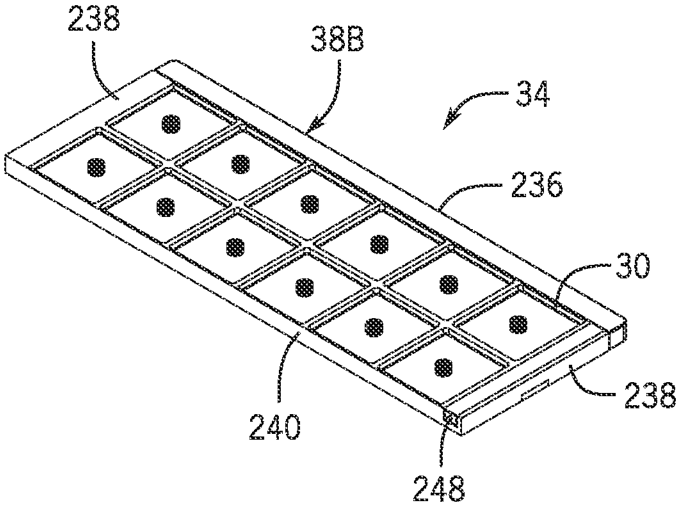
Figure 11C:
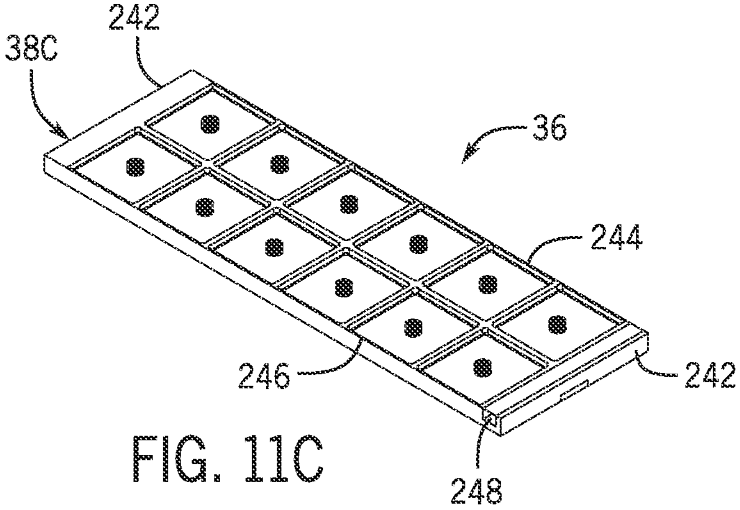
Figure 11D:
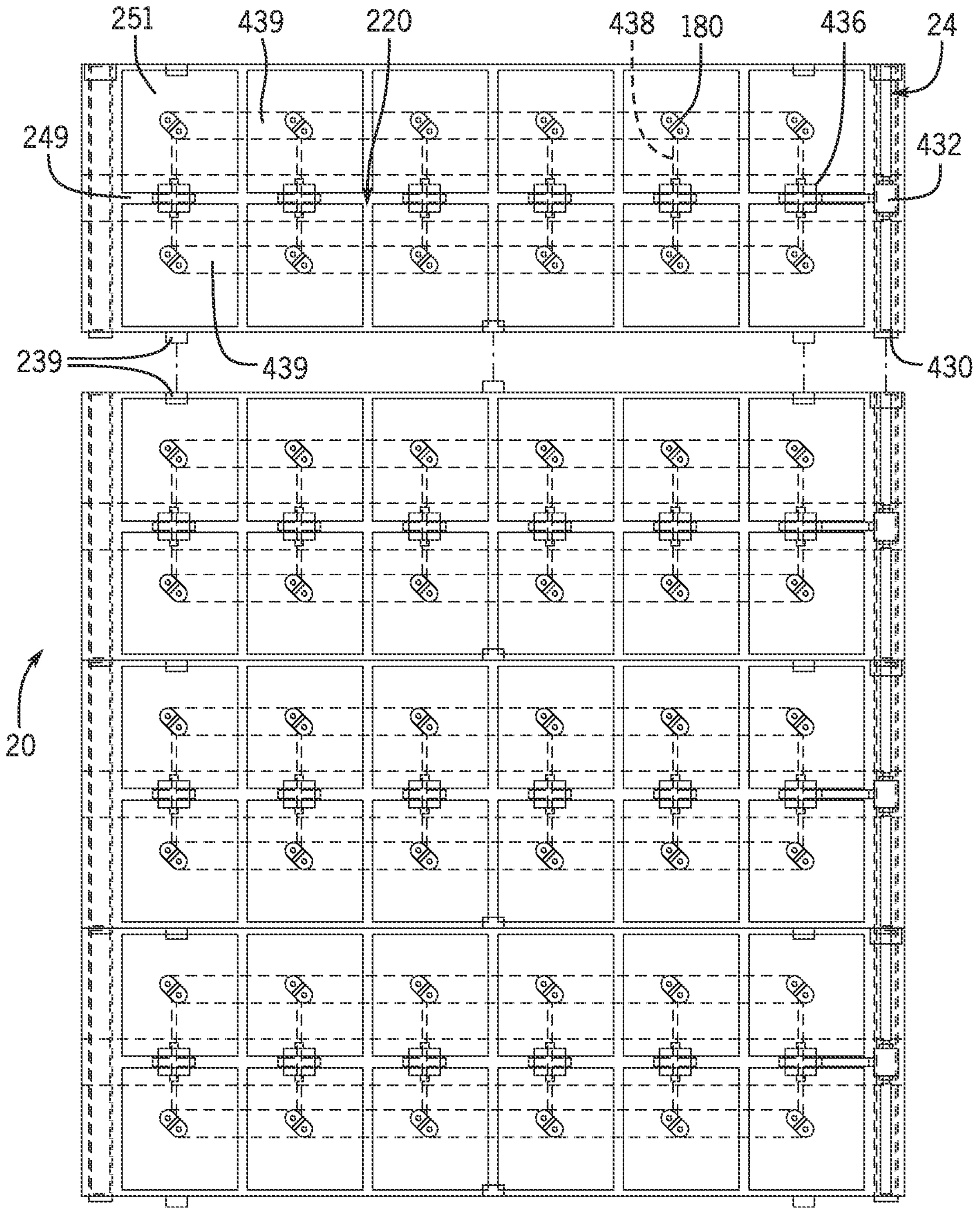
Figure 23:
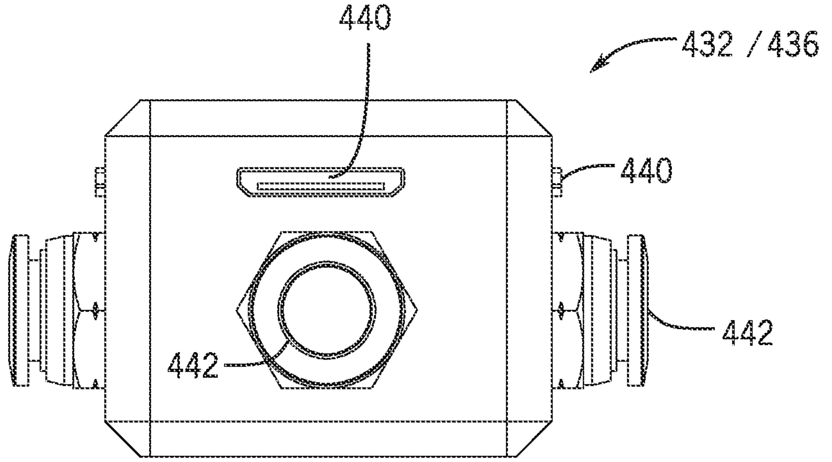
FIG. 23 is a side view of a manifold for use with the base board array of FIG. 11D.
Figure 24:
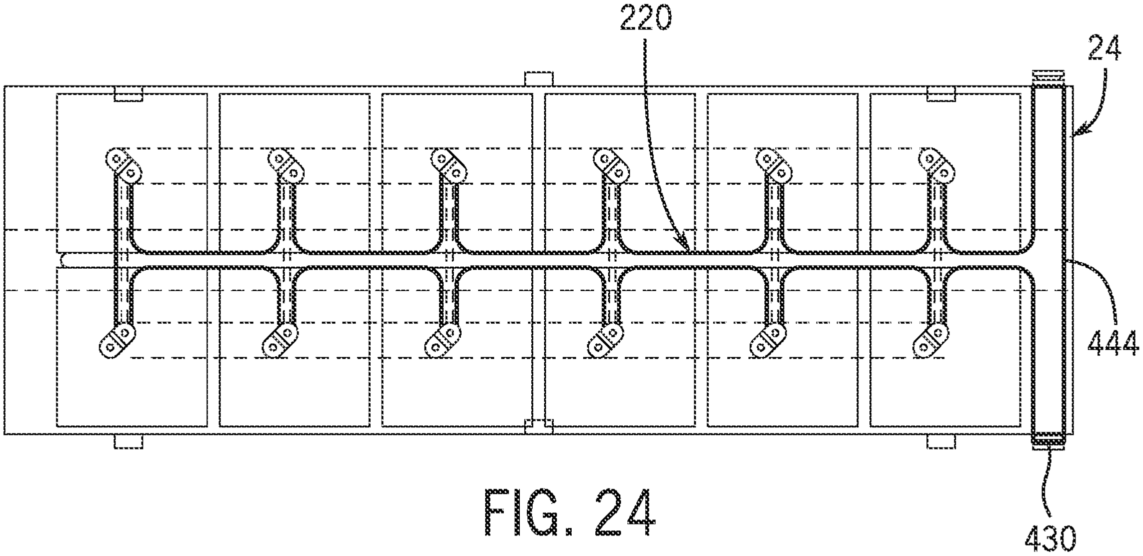
FIG. 24 is a top view of a base board array including a single-piece channel architecture.

In particular, FIG. 9 schematically illustrates air connections 222 from the main unit 26 to the individual cells 18, and data and power connections 224 between the main unit 26 and the individual cells 18. For example, power and data (such as solenoid valve instructions) can be communicated from the main unit 26 to each cell 18, and data (such as sensor data) can be communicated from each cell 18 back to the main unit 26. In some applications, as shown in FIGS. 11D and 23, the connections 222, 224 can be accomplished via a manifold architecture. For example, FIG. 11D illustrates a main line quick connector 430 in communication with a main line manifold 432 through the main line 24, which then branches to sub-line manifolds 436 through the sub-line 220, then to individual cell manifolds (e.g., port interfaces 180) through cell lines 438. As shown in FIG. 23, a manifold (e.g., sub-line manifold 436 or main line manifold 432) can include one or more power and data ports 440 and one or more quick fittings 442. In other applications, as shown in FIG. 24, the connections 222, 224 can be accomplished via a tubing architecture. For example, FIG. 24 illustrates a main line quick connector 430 with a single-piece channel 444 branching from the main line 24, to the sub-line 220, to individual cells. The single-piece channel 444 can be, for example, a plastic or rubber material and can include internal features to hold wiring for data and power exchange, as well as accommodate air movement.

Figure 10:
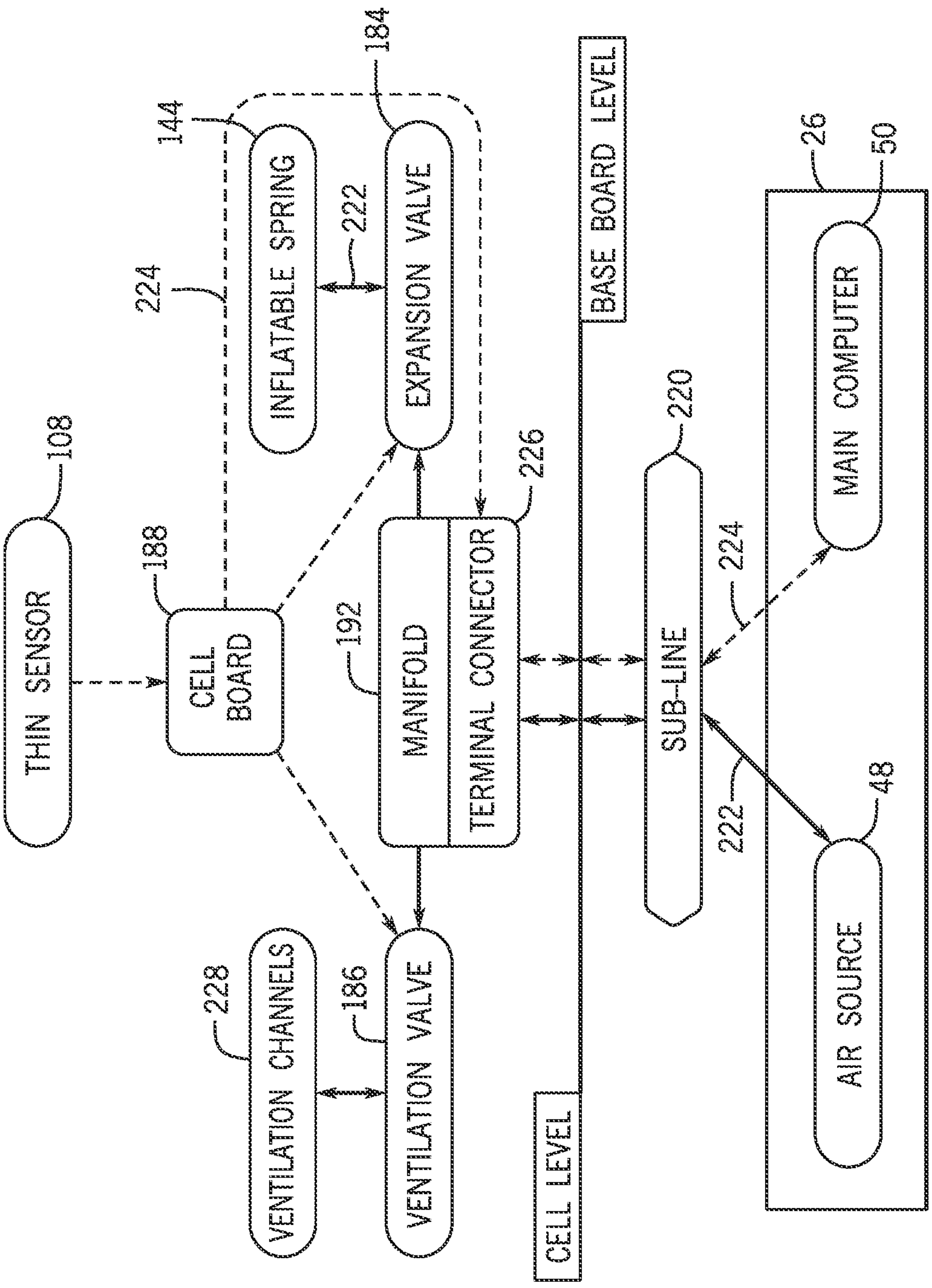
FIG. 10 is a schematic view of an architecture of connections of the patient management of FIG. 1 and the smart cell of FIG. 4.

As a further example, FIG. 10 illustrates a schematic architecture of the connections within an individual cell 18. FIG. 10 illustrates the main unit 26 (with the air source 48 and the main computer 50), and a sub-line 220, providing air connections 222 and data/power connections 224 to the cell 18 via the connection manifold 192 of the cell 18. As shown in FIG. 10, the cell 18 includes the sensor module 108, which can be in communication with the terminal board 188 (e.g., via the sensor cable 136). The terminal board 188 is, in turn, in communication with the connection manifold 192 via a terminal connector 226. Also, the spring activation valve 184 and the ventilation valve 186 are in communication with the terminal board 188 as well as the connection manifold 192. Furthermore, the valves 184, 186 are pneumatically connected to ventilation channels 228 and the spring 144, respectively. The connection manifold 192 is connected, via the base board 30, to sub-lines 220 (as described above with respect to FIGS. 9 and 23-24) that are further connected to the air source 48 and the main computer 50 of the main unit 26.

While the cell 18 is illustrated and described herein as being pneumatically powered with an inflatable spring 144, in other applications, the construction of the cell 18 may include other mechanical devices and mechanisms such as, but not limited to, pneumatic cylinders, linear actuators, hydraulic cylinders, or waters bags as sources of mechanical power to generate positive and negative forces pushing and pulling the mattress layers and user on top of the cell 18. There are many advantages to using the inflatable spring 144 and compressed air such as, for example, fast reaction compared to other systems (e.g., to accomplish sufficient lift as a quick response), air being an unlimited mechanical source of power, the spring portion 102 comprising non-toxic elements, outstanding strength, durability, easy implementation, and comfortability, among other reasons.

Turning now to the base board array 20, as described above, the base board array 20 can comprise multiple individual base boards 30 and acts as the structural component that supports the mattress 12. The base board array 20 structures the mattress 12, supports the cells 18, and links the cells 18 to the electronic and pneumatic systems of the main unit 24. For example, in some applications, the base board array 20 can hold and manage tubing, wiring, and/or air valves.

Furthermore, as described above with respect to FIG. 8, individual base boards 30 can include a "quick connect" port interface 180 configured to snap fit a cell 18 onto the base board 30 in a proper orientation, feed the cell 18 with air from the air source 48, and interconnect the cell 18 with the main computer 50 for data and power transmission. Also, as shown in FIG. 8, to help orient and support the cell 18, each base board 30 can also include a recessed seat 250 sized to match an outer circumference of the platform portion 104 of the cell 18. As a result, the cell 18 can sit within the recessed seat 250 when the cell 18 is connected to the base board 30.

In some applications, the base board array 20 is made up of multiple smaller arrays of individual base boards 30, such as the lower base board array 32, the upper base board array 34, and the intermediate base board array(s) 36. As illustrated in FIG. 11A, the lower base board array 32 can include a frame 38A around three edges (e.g., a lower edge and two side edges) and an "open edge" (e.g., an upper edge 234). Similarly, as shown in FIG. 11B, the upper base board array 34 can include a frame 38B around three edges (e.g., an upper edge 236 and two side edges 238) and an open edge (e.g., a lower edge 240). Furthermore, as shown in FIG. 11C, intermediate base board arrays 36 can include a frame 38C around two opposite edges (e.g., two side edges 242), with two open edges (e.g., upper and lower edges 246, 248). While the arrays 32, 34, 36 are shown and described as having different open and closed edges, in some applications all arrays 32, 34, 36 may be manufactured the same, with additional accessories to "close" off specific edges, differentiating the arrays 32, 34, 36 for upper, lower, or intermediate use.

In some embodiments, as shown in FIG. 11D, each base board array 32, 34, 36 can include a support bar 249, such as an aluminum or other material bar to help reinforce the baseboard structure and minimizing bending under stresses as well as individual cell nests 251 to frame and hold cells 18. Each base board array 32, 34, 36 can include a main line 24, a sub-line 220, a cell line 438, as well as a main line connector 430, as discussed above. Furthermore, in some applications, as shown in FIG. 11D, each base board array 32, 34, 36 can include exhaust channels 439 running underneath the arrays 32, 34, 36 to help evacuate air from the cells 18 to the environment.

To create the base board array 20, the lower base board array 32 and the upper base board array 34 can be arranged so that their respective open edges 234, 240 align and the frame sections 38A, 38B engage at one or more side edges 232, 238, thus creating a frame 38 entirely around the base board array 20 (or at least along both sides of the base board array 20). When aligned, the lower base board array 32 and the upper base board array 34 can be coupled together, for example, via straps, snap joints 239 (shown in FIG. 11D), or other connection mechanisms. The intermediate base board arrays 36 are modular components capable of adding length to the base board array 20, thus permitting constructing a larger system 10 when desired. Accordingly, to create a larger base board array 20, one or more intermediate base board arrays 36 can be arranged and coupled between the lower base board array 32 and the upper base board array 34, so that respective open edges 234, 240, 244, 246 align and frame sections 38A, 38B, 38C along one or more of the side edges 232, 238, 242 are coupled together to create a frame 38 entirely around the base board array 20. Additionally, in some applications, an accessory (not shown) can be coupled to both ends of the base board array 20 to help prevent sliding inside the frame 28 when the mattress 12 is assembled.

Figure 11E:
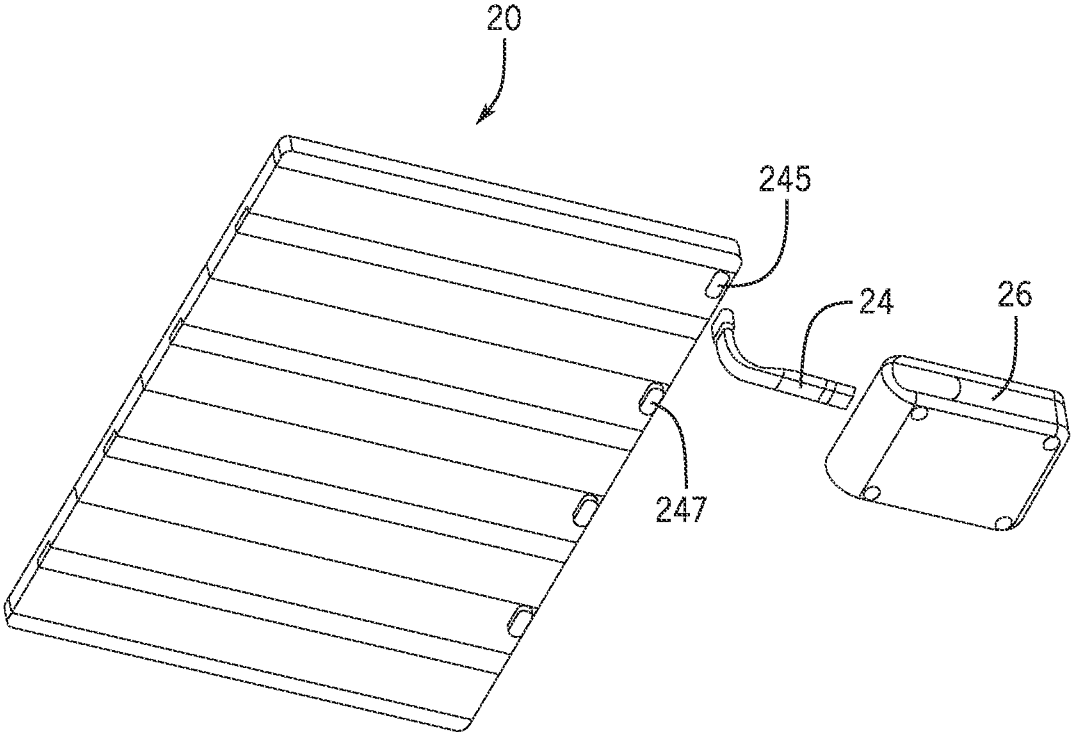

In some applications, the base board frame 38 can be generally enclosed, with at least one side thereof forming a conduit for electrical and/or pneumatic connections. While the base board frame 38 may include conduits along both sides, in some applications, only one side may be considered an "active" side providing a conduit for connections. However, in other applications, both sides may be active. For example, FIGS. 11B and 11C illustrate conduit openings 248 at open edges of the frame sections 38B, 38C, as shown in FIGS. 11B and 11C. In this manner, when assembling the base board array 20, the conduit openings 248 can be aligned to form a single conduit throughout at least the side of the frame 38. Additionally, as shown in FIG. 11E, at least one of the base board arrays 32, 34, 36 can include a source connector 245 configured to engage the main line 24 which, in turn, connects the base board array 20 to the main unit 26. For example, each base board array 32, 34, 36 can include a source connector 245, through unused source connectors 245 can include a covering 247 to disable the connector 245.

While the individual base boards 30 and any connections therebetween on a base board array 32, 34, 36 may be formed of plastic (though other materials may be contemplated), in some applications, the base board frame 38 may be formed of metal, such as stainless steel, aluminum, or structural fibers such as carbon fibers. In this manner, the base board frame 38 can structurally reinforce the base board array 20, keeping the form and structural integrity of the array 20.

With further reference to the main unit 26, in some applications, the main unit 26 can include a housing 260, as shown in FIGS. 1-2, that encloses the air source 48 and the main computer 50. The air source 48 can be a centralized source of air to power movement of the cells 18. In one example, the air source 48 can be a compressor or air pump powered by electricity, and including a compressor tank, regulators, gauges, check valves, pressure sensors, feed lines, directional valves, and/or other components (not shown) to distribute and manage feed lines and connections between components. However, in other applications, the air source 48 may be replaced with another component configured to generate positive or negative movement of the cells 18.

The housing 260 of the main unit 26, by enclosing the air source 48, can help reduce the sound and vibrations created by the air source 48. Also, as shown in FIG. 2, the housing 260 can include air vents 262 and associated filters (not shown) aligned with the air vents 262 to avoid impurities entering the main unit 26, a power button 264, and the main line 24.

Figure 12:
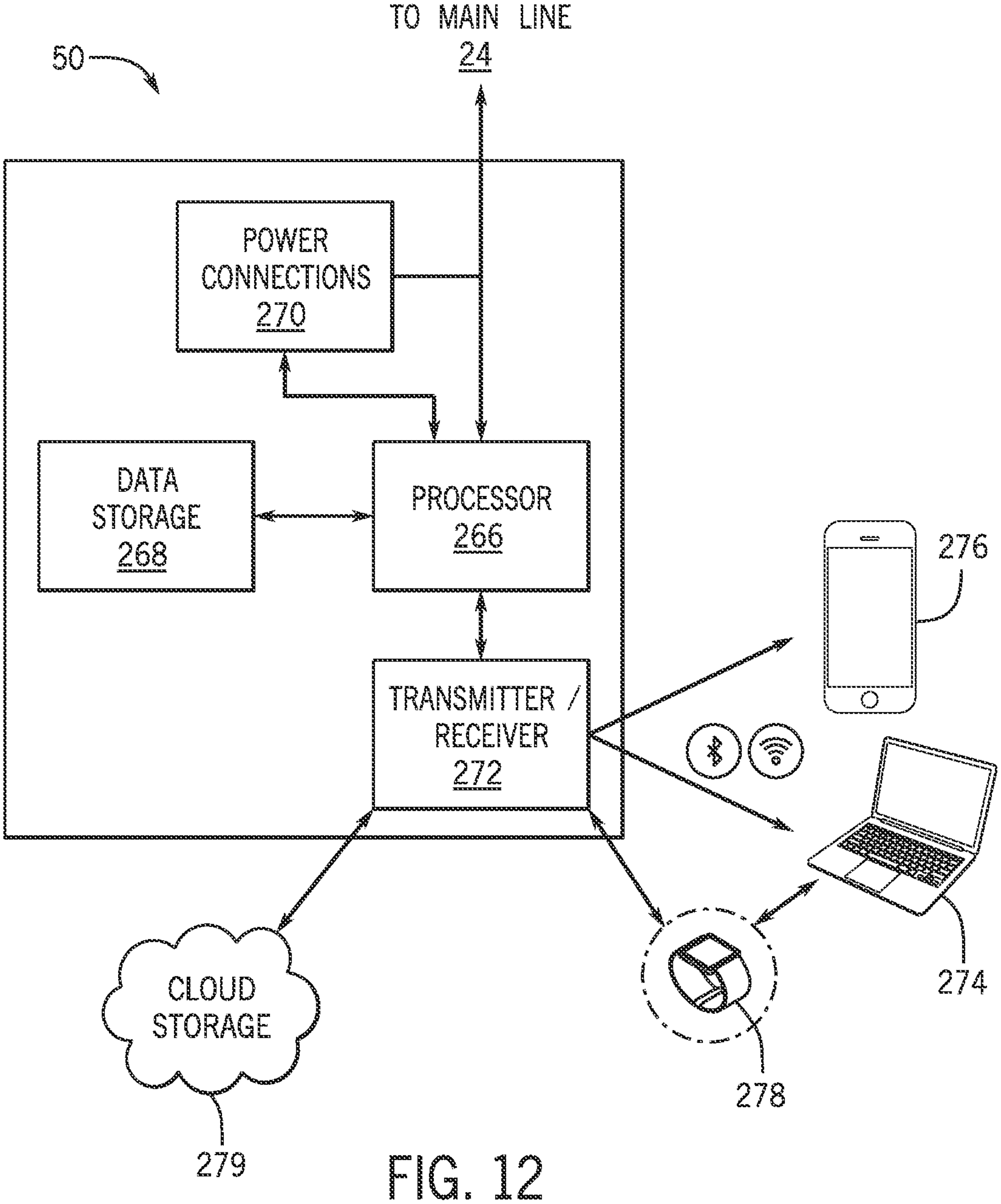
FIG. 12 is a schematic representation of a main computer for use with the patient management system of FIG. 1.

Additionally, as shown in FIG. 12, the main computer 50 can include a processor 266, data storage 268, power connections 270, and a transmitter/receiver 272. For example, the processor 266 can execute programs or algorithms configured to send power (via the power connections 270) to the cell array 16, receive data from the cell array 16, including measurements of sensed user biomarkers, analyze the data (as further described below), and send commands to selectively pneumatically power individual cells 18 in response to the analysis. The processor 266 can further store the sensed data and/or analyses and/or commands executed via the data storage 268, or retrieve user profiles or other stored data or programs from the data storage 268. Additionally, the processor 266 can send or retrieve data via the transmitter/receiver 272, which may be a wired connection to one or more external components, or a wireless transmitter/receiver, such as Bluetooth or WiFi. For example, while the main computer 50 includes the data storage 268, the main computer 50 can also send to or receive from cloud storage 279 via the transmitter/receiver 272. Additionally, the main unit 26, via the transmitter/receiver 272, can interface with an external computer 274, phone application 276, or wearable device 278 to provide data, deliver alerts, and/or receive data or instructions. As a result, the external computer 274, phone 276, or wearable device 278 can act as a user interface of the system 10.

For example, a notification system flow may have several methods of distribution between the main computer 50 and the user interfaces. For example, information can flow from a wearable device 278 to the main computer 50, from the wearable device 278 to a user's phone 276 and from the phone 276 to the main computer 50, from the wearable device 278 to the user's family member's phone 276 and from the phone 276 to the main computer 50, from the wearable device 278 to the user's computer 274 and, through internet and a home router, to emergency services, and then to the main computer 50. Any combination of the above examples may be contemplated in some applications. This multiple signal input alert protocol can secures a response of the system 10, the activation of the mattress 12, and alert family or emergency services for further assistance, if needed.

With respect to wearable devices 278, in some applications, existing epileptic wearables devices can be linked to the main computer 50 to activate the mattress 12 in case, for instance, of a generalized seizure that requires immediately repositioning of the patient to a recovery position. The wearable device 278 can be used to recognize the seizure and send a signal alert or notification directly to the main computer 50, which can process the data, along with other sensed data, and activate patient repositioning autonomous, as well as send alerts and/or stimulate the patient.

Figure 13:
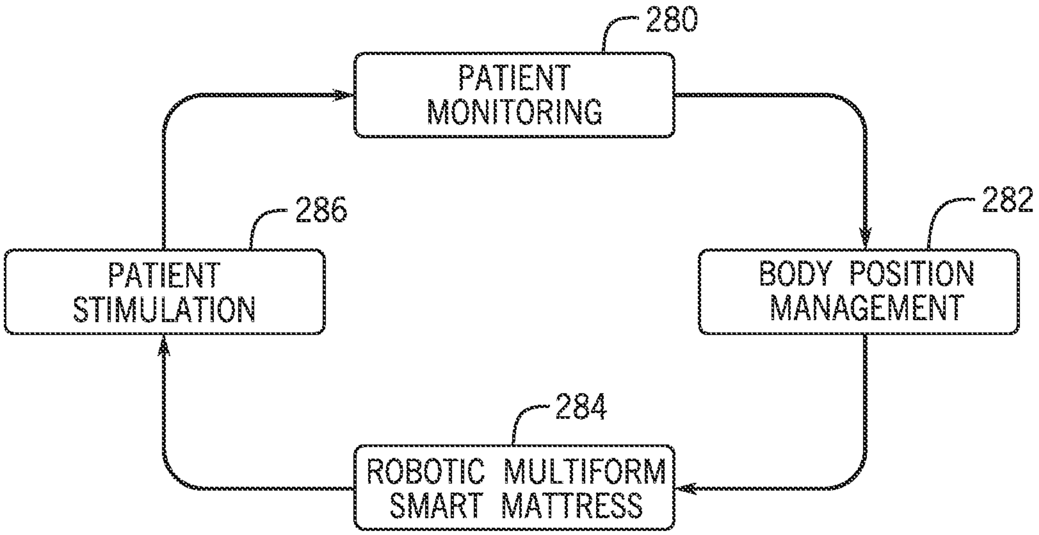
FIG. 13 is a schematic view of a basic architecture of the patient management system of FIG. 1.

Accordingly, when the system 10 is assembled, as described above, an extended sensing and repositioning surface of interconnected cells 18 is formed to monitor a user and intervene, if necessary. For example, FIG. 13 illustrates a basic architecture of the system 10. As shown in FIG. 13, the system 10 includes patient monitoring 280, body position management 282, smart mattress adjustment 284, and patient stimulation 286.

Figure 14:
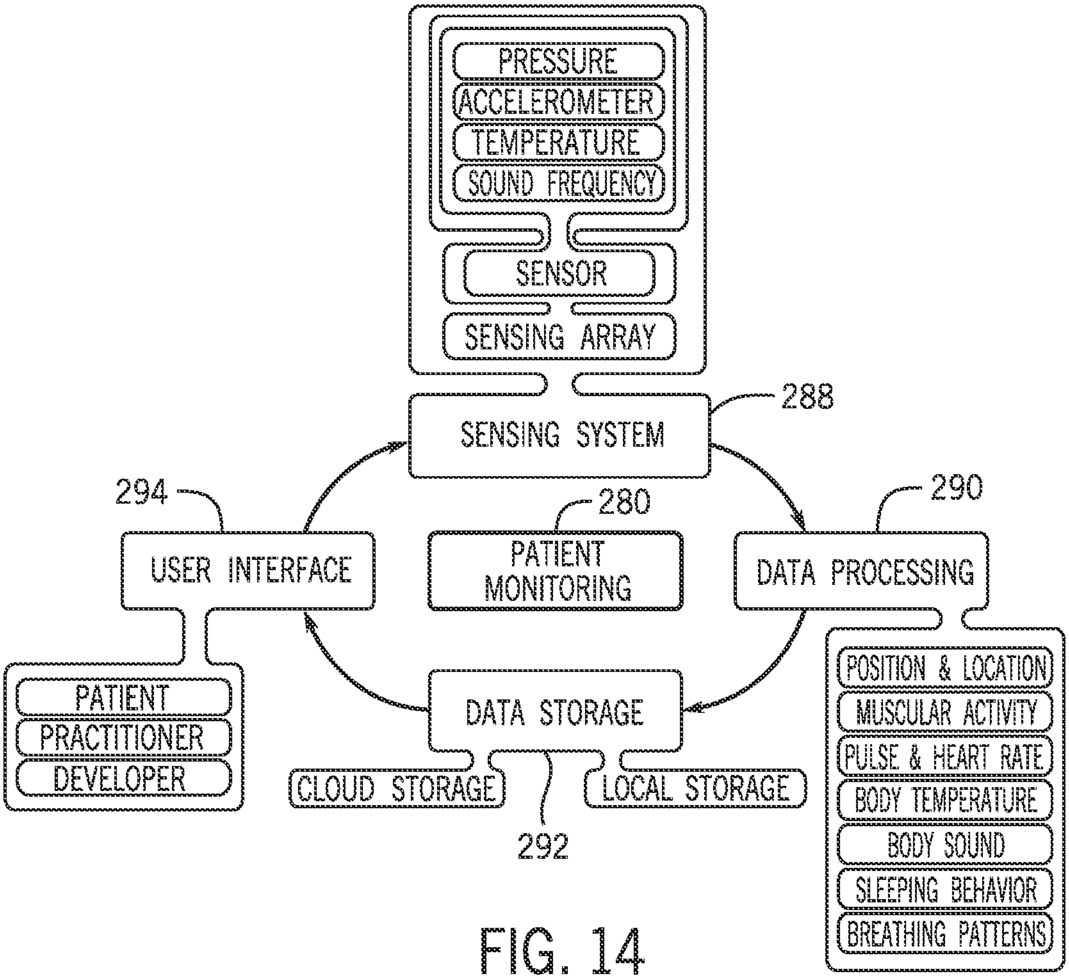
FIG. 14 is a schematic view of a patient monitoring component of the patient management system of FIG. 1.

FIG. 14 illustrates components of the system 10 involved with the patient monitoring component 280 (or sensing portion) of the system 10. In particular, as shown in FIG. 14, patient monitoring 280 involves a sensing system 288 (e.g., the sensor module 108 with various sensors, described above), data processing 290 (e.g., via the processor 266 of the main computer 50 or an external computing component in communication with the main computer 50), data storage 292 (such as cloud storage 279 or local data storage 268 of the main computer 50), and a user interface 294 (e.g., via the external computer 274, phone 276, and/or wearable device 278 described above, or another device).

With further reference to the data processing component 290, as shown in FIG. 14, biometric data associated with data processing for patient monitoring can include, but is not limited to, user position and location, muscular activity, pulse and heart rate, body temperature, body sounds, sleeping behavior, and/or breathing patterns. This biometric data may be receives from the sensing system 288, the data storage 292, and/or the user interface 294.

With respect to the user interface 294, it should be noted that one or more user interfaces may be associated with the user, a practitioner, and/or a developer. Example user interfaces include, but are not limited to, an external computer 274, a phone 276, and/or a wearable device 278, as described above. For example, the system 10 can create models based on monitored data and such models can be projected and visualized digitally through one or more of the user interfaces (e.g., via an application on the user interface).

Figure 15:
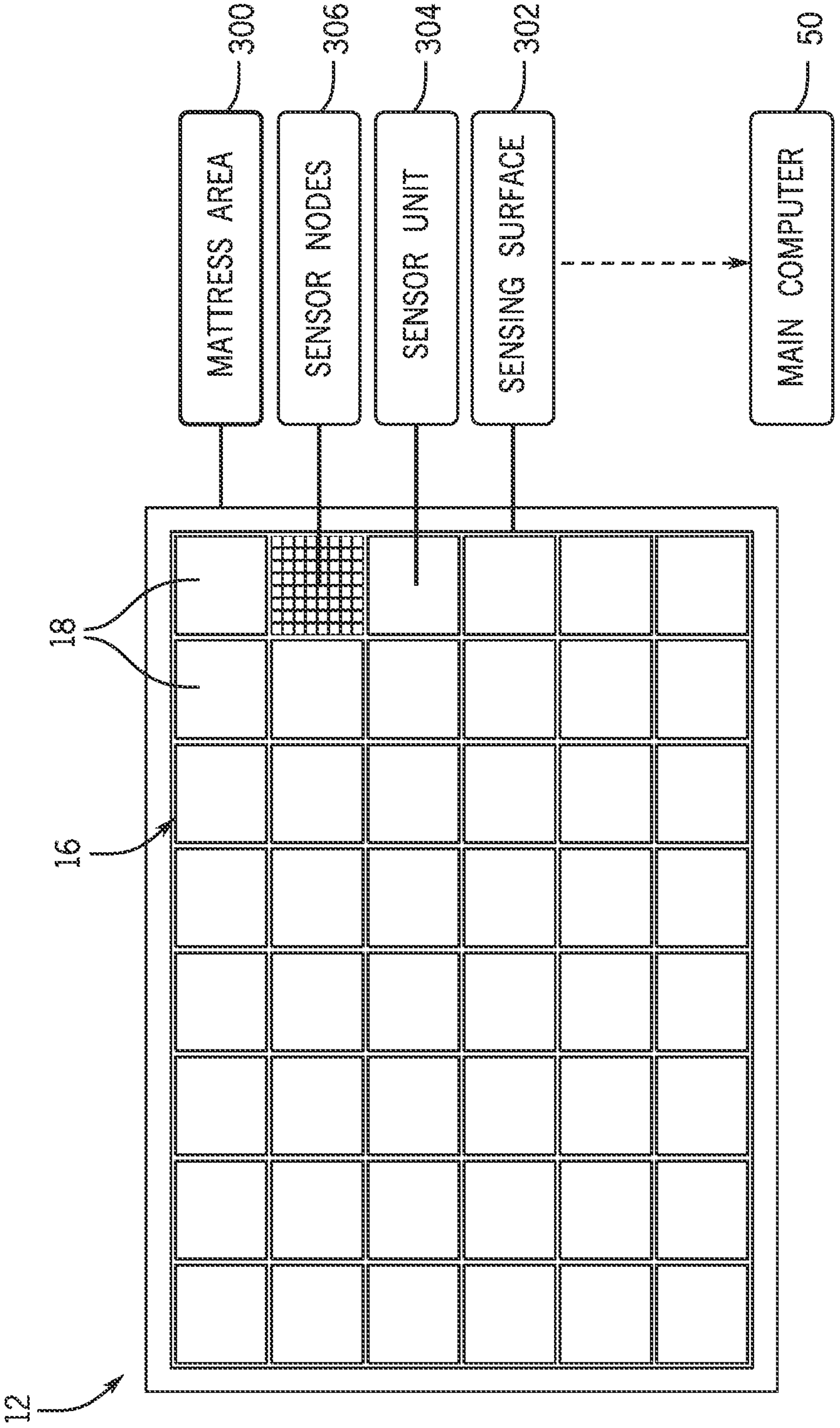
FIG. 15 is a top view of a mattress and associated connections of the patient management system of FIG. 1.

With further reference to patient monitoring component 280 and, in particular, the sensing system 288, FIG. 15 illustrates an example top view of the mattress 12. Within a mattress area 300 (corresponding to the mattress pad 14) is a sensing surface 302. Within the sensing surface 302 is an individual sensor unit 304 of each cell 18. Within each sensor unit 304 is an array of sensor nodes 306 (such as sensor nodes 122 described above with respect to FIG. 7). The sensing surface (e.g., comprised of sensor units 304 of sensor nodes 306) is in communication with the main computer 50.

Figure 16A:
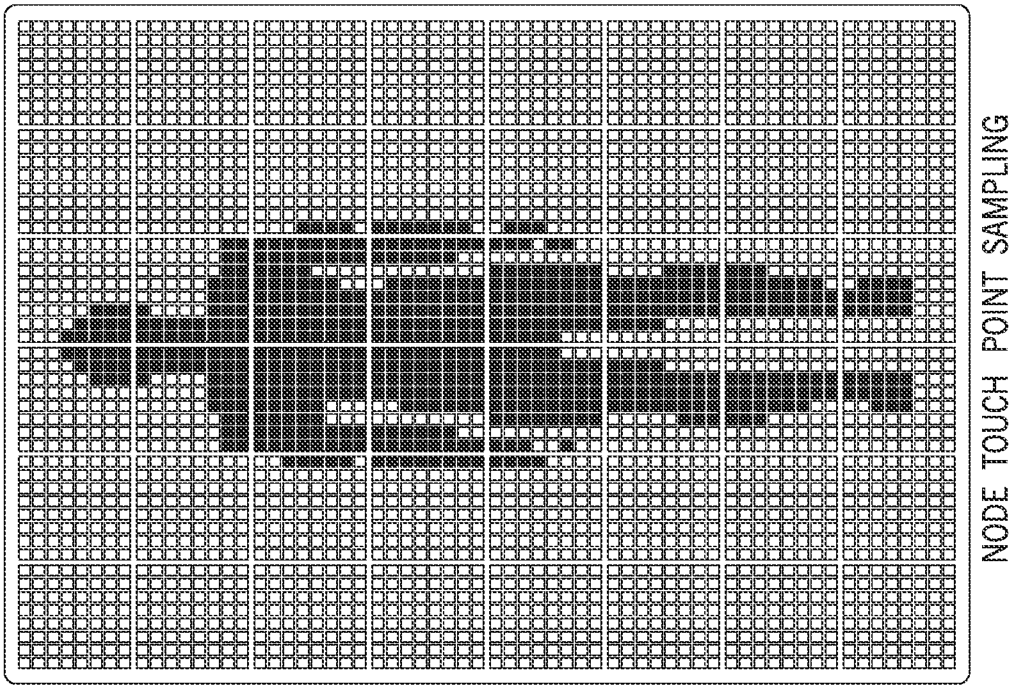
FIG. 16A is an example node touch point sampling from a sensor array of the patient management system of FIG. 1.
Figure 16B:
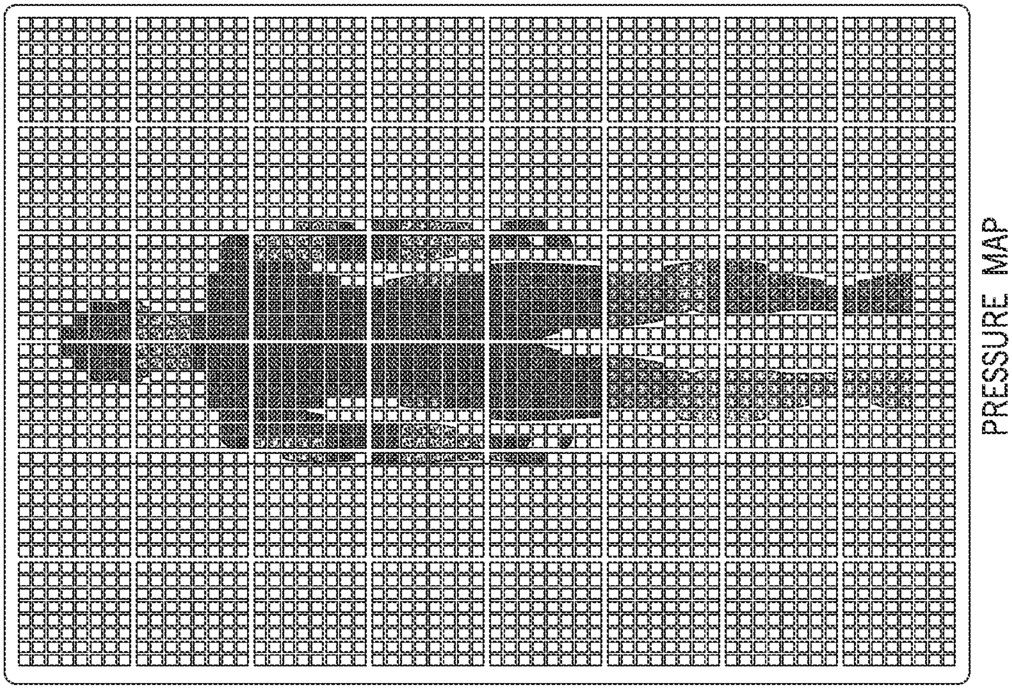
FIG. 16B is a pressure map created from the node touch point sampling of FIG. 16A by a main computer of the patient management system.

For example, FIG. 16A illustrates a node touch point sampling of pressure readings from individual nodes 306. These pressure readings can be communicated to the main computer 50 in the main unit 26 which, in turn, can analyze the data and create a pressure map, as shown in FIG. 16B. Similar analysis can be executed by the main computer 50 for other user metrics besides pressure, such as movement, temperature, sound, humidity, etc.

Figure 17:
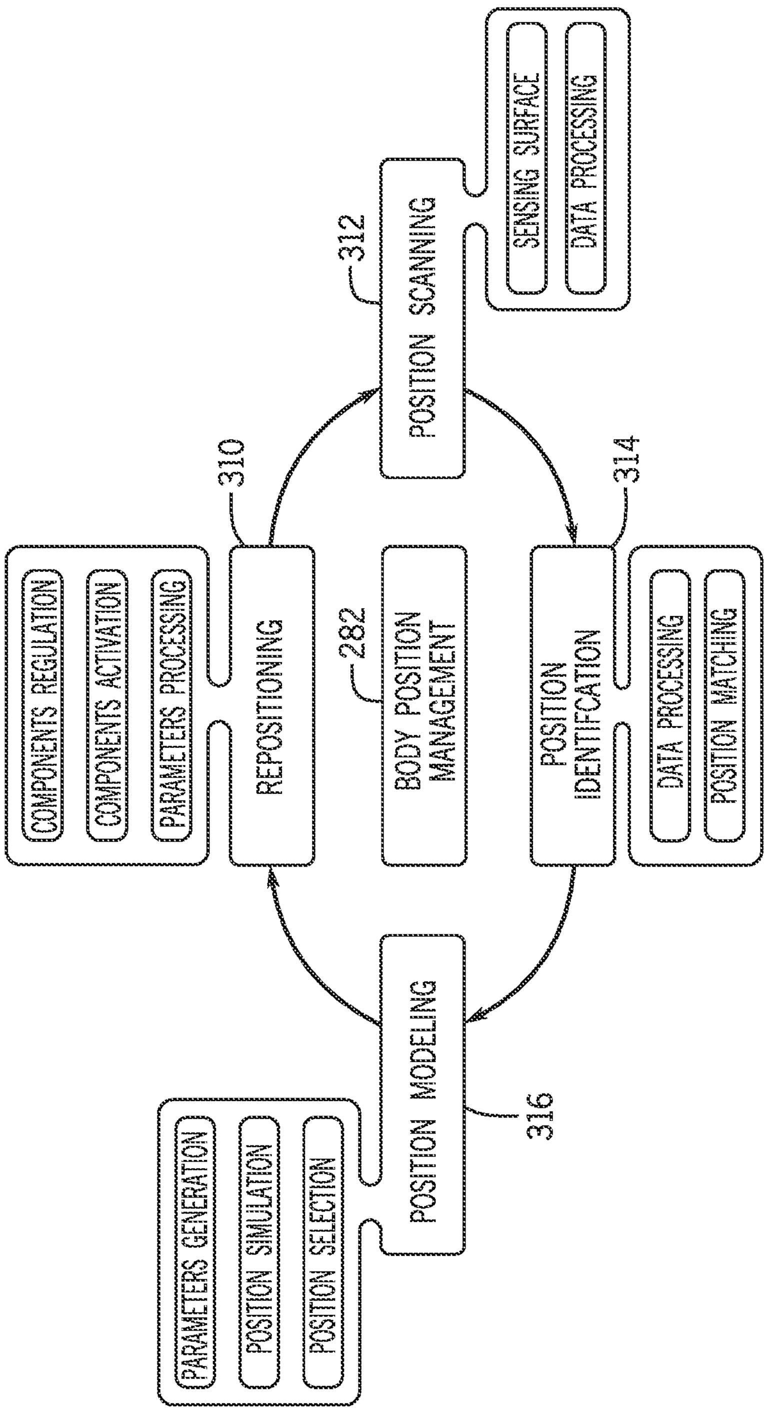
FIG. 17 is a schematic view of a body position management component of the patient management system of FIG. 1.

With further reference to the body position management component 282 of the system, FIG. 17 illustrates components of the system 10 associated with body position management. In particular, FIG. 17 shows a repositioning component 310, position scanning 312, position identification 314, and position modeling 316. The repositioning component 310 can involve components regulation and activation (e.g., associated with the spring portion 102 of individual cells 18), and parameter processing. Position scanning 312 can reference the sensing surface 302 described above as well as data processing. Position identification 314 can incorporate data processing and position matching (e.g., to identify a present position of the user on the mattress 12). Position modeling 316 can involve generating parameters, simulating positions, and selecting a model position for the user.

Figure 18:
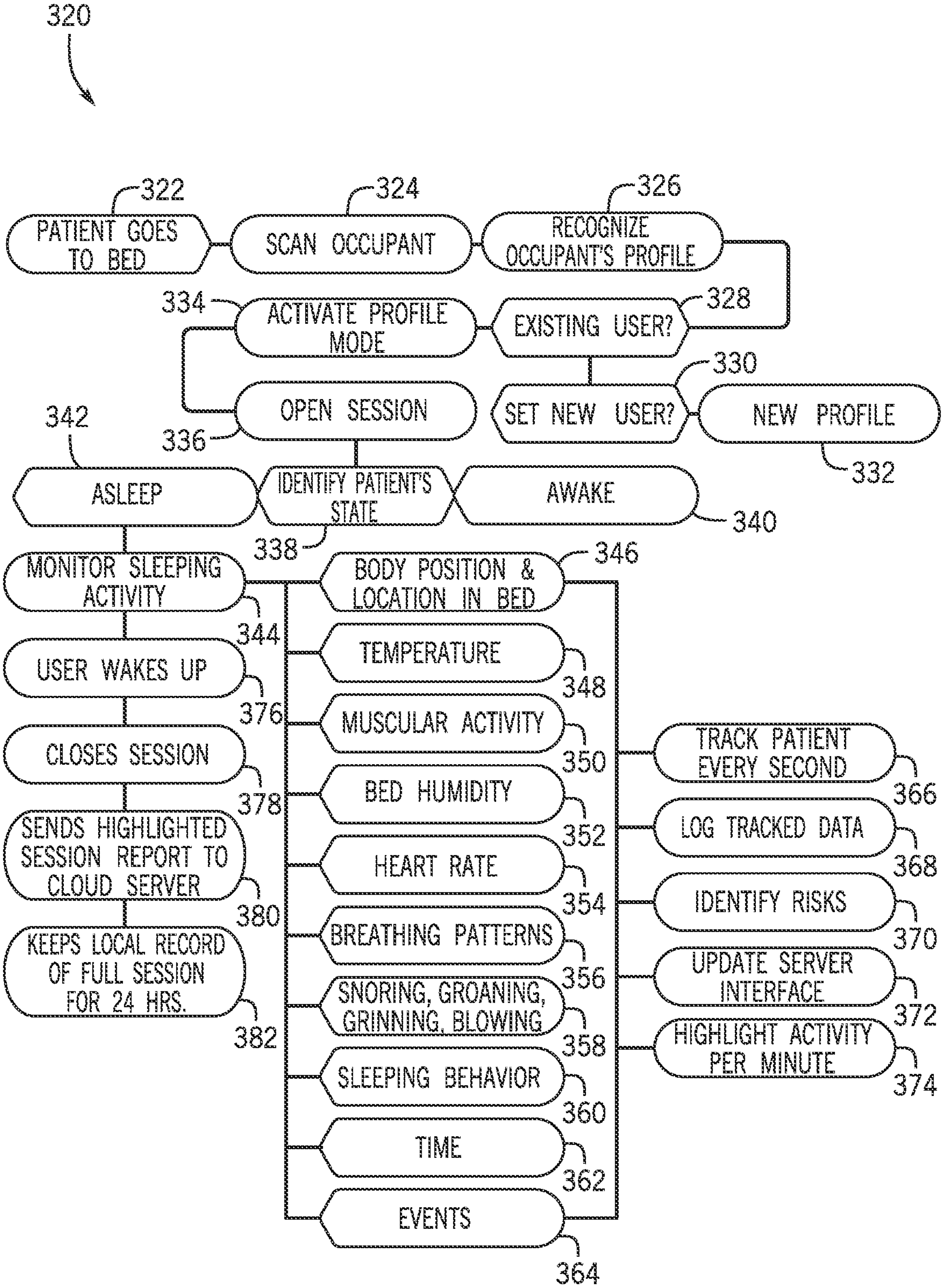
FIG. 18 is a monitoring process associated with the patient management system of FIG. 1.

By way of example, FIG. 18 illustrates a monitoring process 320 associated with at least the patient monitoring and body position management components 280, 282. Once a user lies on the mattress 12 for sleep (block 322), the system 10 will scan the user (block 324) and attempt to recognize the user's profile (block 326). If the system 10 does not recognize the user's profile as an existing user (at block 328), the system 10 sets a query to set a new user (block 330), and creates a new user profile (block 332). If the system 10 does recognize the user's profile (at block 326), the system 10 activates the profile mode associated with that profile (block 334) and opens a new session for that profile (block 336).

The system 10 then identifies the patient state a block 338: awake (block 340) or asleep (block 342). If asleep, the system monitors the user's sleeping activity (block 344). Such monitoring can include body position and location in bed (block 346), temperature (block 348), muscular activity (block 350), bed humidity (block 352), heart rate (block 354), breathing patterns (block 356), snoring, groaning, grinning, or blowing (block 358), other sleeping behavior (block 360), time (block 362), and specific events (block 364). These monitored parameters, e.g., via the processor 266 of the main computer 50, can be tracked at specific time intervals, such as every second (block 366), and logged (block 368). Additionally, the processor 266 can analyze the parameters to identify risks (block 370), update user interface(s) (block 372), and highlight certain activity, such as at the user interfaces, at specific time intervals, such as every minute (block 374).

While the system 10 monitors sleeping activity at block 344, if the user wakes up (block 376), the monitoring session is closed (block 378). A session report including monitored metrics or other data or analysis based on the monitored parameters can be sent to cloud storage 279 (block 380) and/or can be saved to local storage (block 382), for example, for a time period such as 24 hours.

Accordingly, the system 10 can provide a parametric biosensing surface on an upper layer of a mattress 12, generated by linking individual cells 18 to each other and forming a network of sensing devices, for monitoring a user's activity in bed. As noted above, this activity may include, but are not limited to, position, temperature, muscular activity, body pressure areas, and activities and patterns in bed. As every cell 18 includes a sensing surface, such monitoring can be precisely mapped to the user's body. For example, every cell 18 holds an absolute position establishing a parametric network that addresses the logical communication and physical connectivity of the sensors. The main computer 50 can access, integrate and distribute sensor data, manage large data storage, distribute the data, and perform intensive data computation about the patients' activity. As such, the monitored data can be used to develop precise and individualized computational models to predict emergency events, such as seizures or other emergency conditions, occurring in bed. The models may also be used as a research tool, for example, to better assess risks, understand seizures in bed, and monitor overall patient's sleeping health. Furthermore, the monitored data can be used to determine when intervention is necessary, and the system 10 can autonomously perform such intervention without human assistance. In some applications, the monitored data can also be sent to a practitioner, who can then control interventions remotely and in real time.

For example, with respect to smart mattress adjustment component 284 of the system 10, generally, based on patient monitoring and body position management components 280, 282, the main computer 50 can determine if and how the user needs repositioning and individually control cells 18 to accomplish the specific repositioning. That is, by controlling the springs 144 of individual cells 18, the main computer 50 can raise portions of the mattress 12 to move the user to a desired position.

In other words, the segmentation created by the array 16 of individual cells 18 generates a parametric surface that enables actions or tasks on targeted areas on the user. The parametric surface enables the formation of firm functional topologies on the sleeping surface of the mattress 12, forming forms or protuberances beneficial for the user. The height and angle of these topologies may vary depending on the size and features of the cell 18. These dynamic sections can be adjusted to regulate and control specific areas of the mattress 12 manually or automatically to reduce or increase the level of interaction with the user's body, resulting in a bed topology that modifies patient position on a specific angle, in specific positions, without human supervision.

Figure 19A:
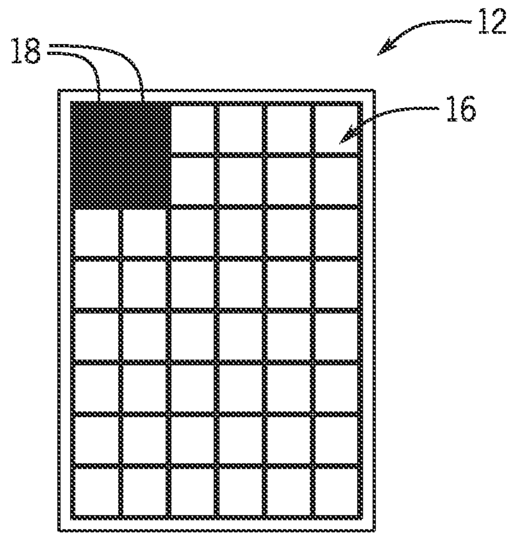
FIG. 19A is a schematic view of a mattress of the patient management system of FIG. 1
Figure 19B:
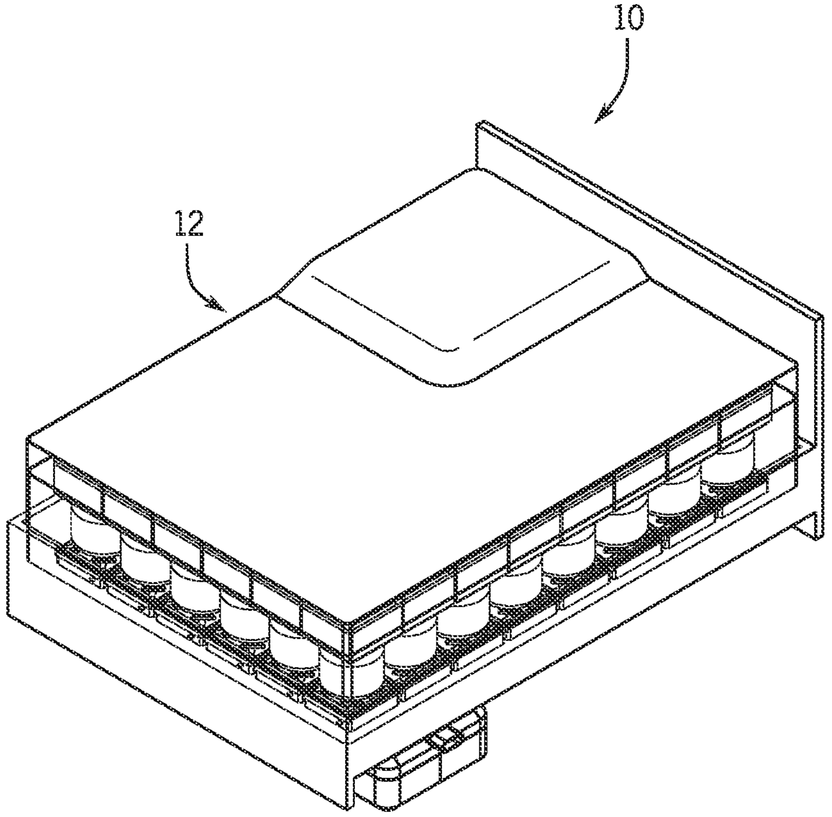
FIG. 19B is a perspective, topographical representation of the mattress of FIG. 19A.
Figure 20A:
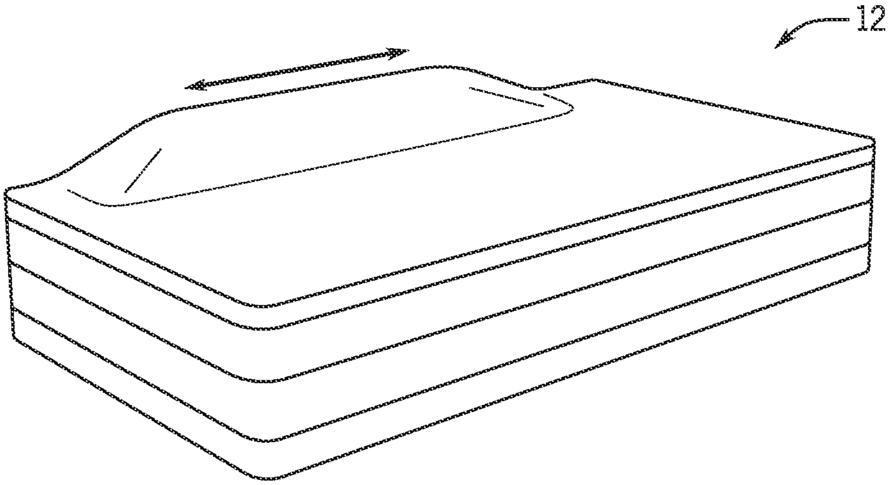
FIG. 20A is a mattress of the patient management system of FIG. 1, configured with a first example topology.
Figure 20B:
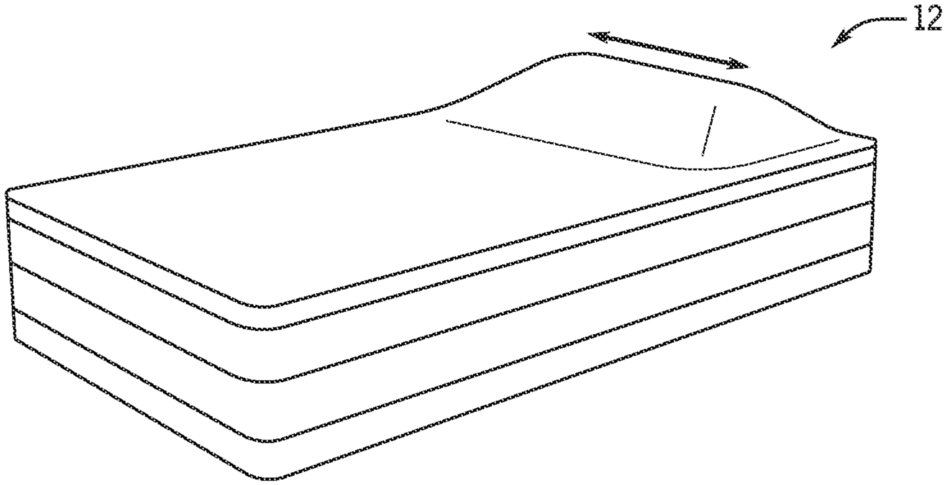
FIG. 20B is the mattress configured with a second example topology.
Figure 20C:
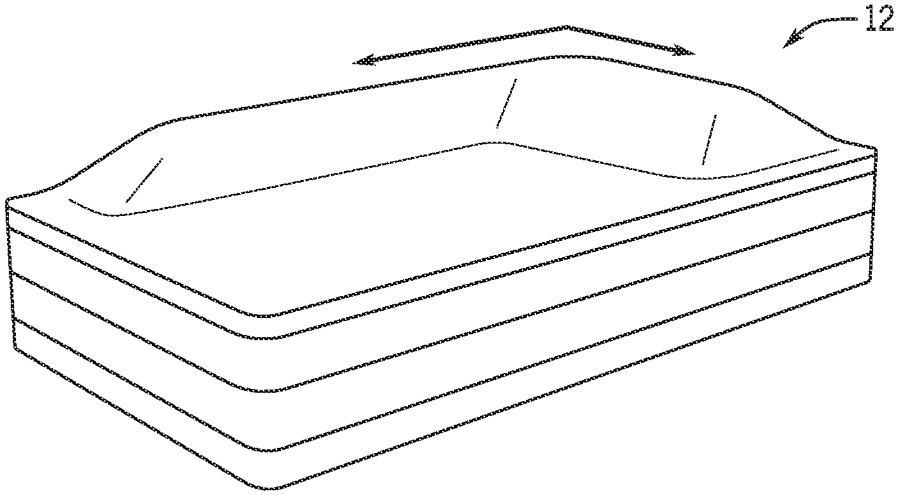
FIG. 20C is the mattress configured with a third example topology.
Figure 20D:
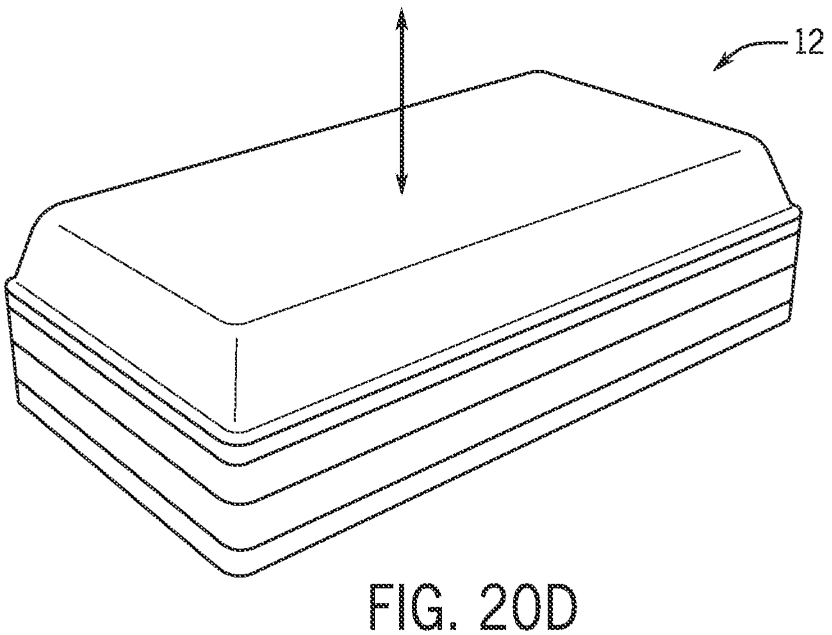
FIG. 20D is the mattress configured with a fourth example topology.

By way of example, FIG. 19A shows a schematic view of the mattress 12, in which four cells 18 are activated, that is, their springs 144 are expanded to vertically raise the cells 18 (as shown by shading). FIG. 19B illustrates a mattress topology view of those four activated cells 18. As another example, FIGS. 20A-20D illustrate further mattress topologies of activated cells 18. In FIG. 20A, a line of cells 18 along an x-axis are activated. In FIG. 20B, a line of cells 18 along a y-axis are activated. In FIG. 20C, a block of cells 18 along both x- and y-axes are activated. In FIG. 20D, all cells 18 in the mattress 12 are activated, with some cells 18 in a positive Z direction and other cells in a nominal Z position or negative Z direction, creating a negative ZYX topology that forms a "nest" for a user.

Accordingly, by providing the array 16 of individual cells 18, the system 10 can accomplish numerous specific topologies in any direction. Furthermore, in some applications, the size and extension of each cell 18 may vary and may be built depending the need of the targeted user. For example, a smaller cell 18 can increase the possibilities to target smaller areas on the user's body or assist smaller body types, such as infants. Furthermore, in some applications, the cells 18 may incorporate additional air bags (not shown) to provider a higher total lift height, generating higher forms and angles.

Figure 21:
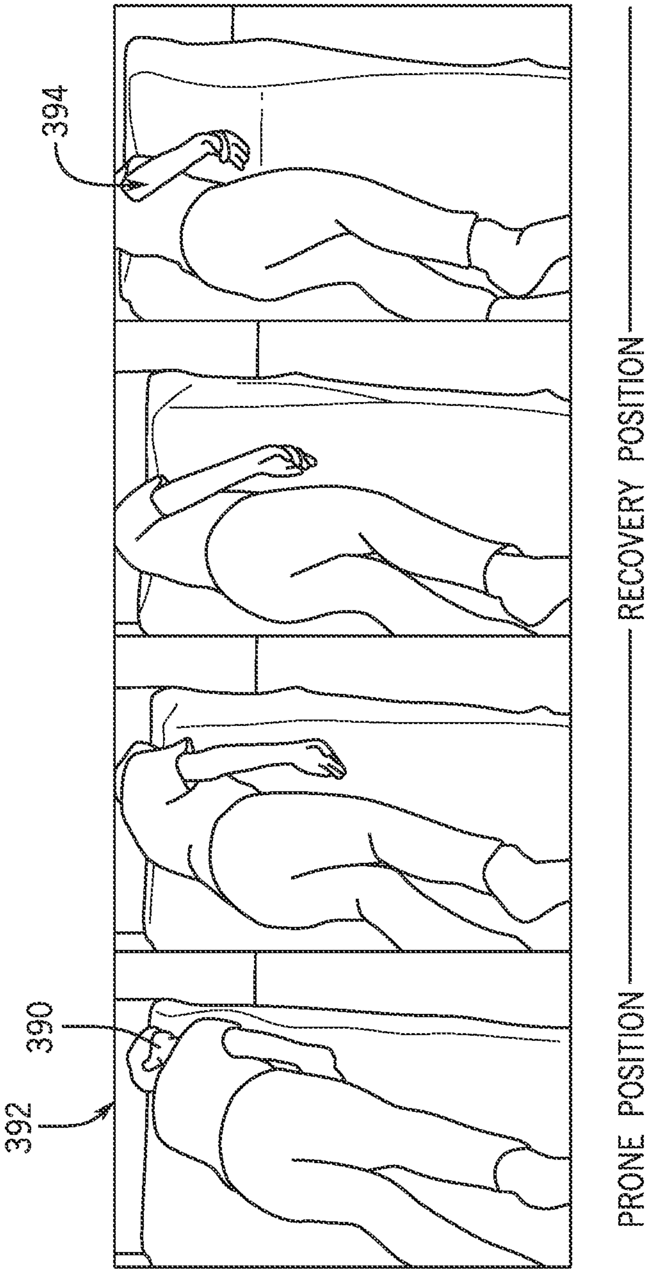
FIG. 21 illustrates various views of a user being moved from a prone position to a recovery position by the patient management system of FIG. 1.

In some applications, the mattress 12 can be configured to reposition a user into a "recovery" position on their side. For example, more than 80% of SUDEP patients are found in a prone (face-down) position after having a seizure overnight. However, a side recovery position is a safer position during a postical (post seizure) state. Thus, as shown in FIG. 21, the mattress 12 can be configured to reposition a user 390 from a prone position 392 to a recovery position 394 during or after a seizure (or at another time while the user sleeps). In some applications, the mattress 12 can be configured to control individual cells 18 in order to turn the user 390 from the prone position 392 to the recovery position 394 (without human intervention) within a specific time period, such as less than 30 seconds or less than 20 seconds.

In addition to repositioning a user, for example, to prevent the prone position or move the user into the recovery position after a seizure, the system 10 may be configured to monitor the user's health, including determining when a seizure is occurring, provide alerts when users are at risk, and stimulate users. For example, FIG. 22 illustrates a method 400 for using the system 10, incorporating patient monitoring 280, body position management 282, smart mattress adjustment 284, and patient stimulation 286.

Figure 22:
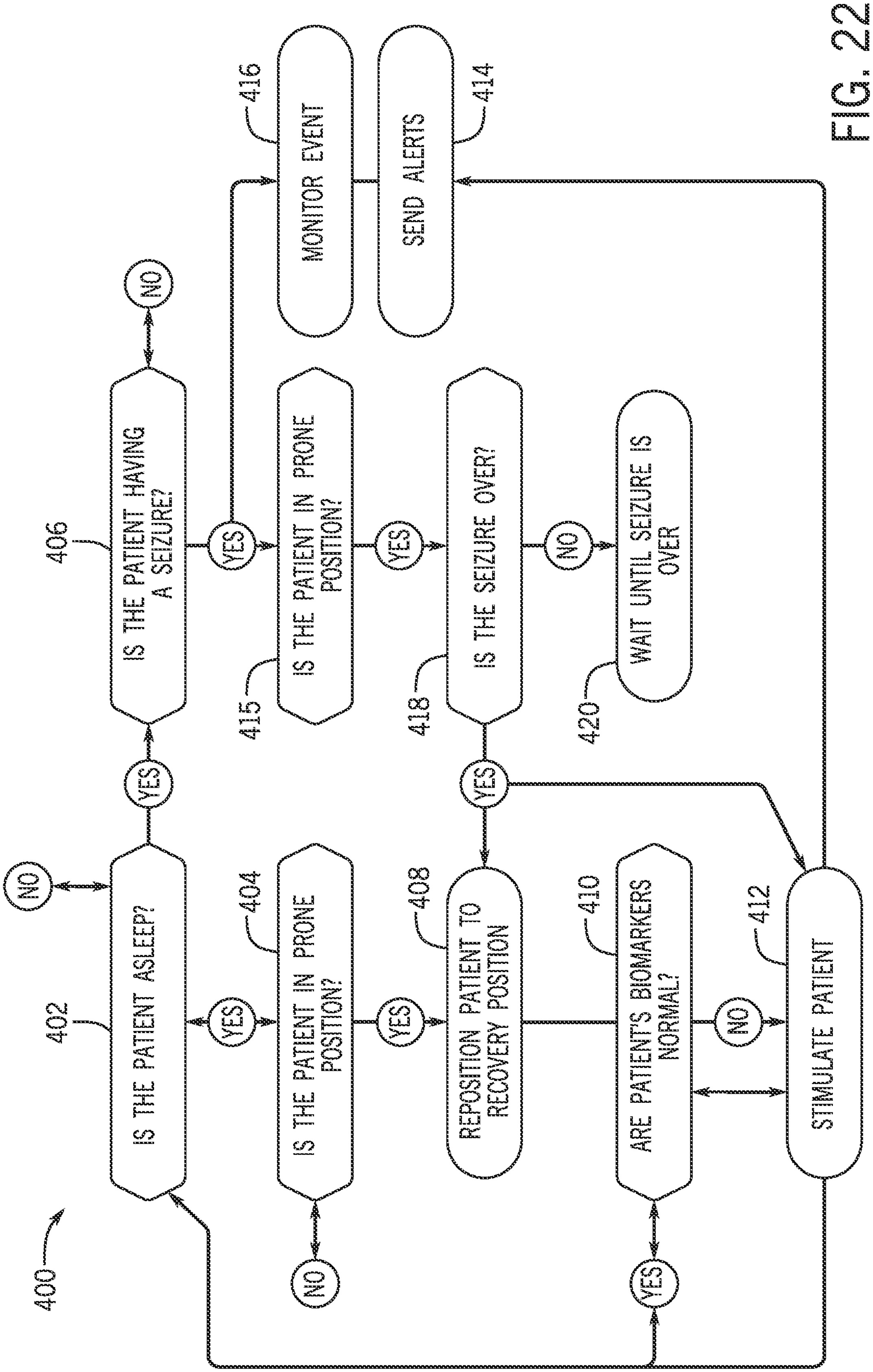
FIG. 22 illustrates a method carried out by the patient management system of FIG. 1.

As shown in FIG. 22, at step 402, the system 10 determines whether the patient is asleep, and the step is repeated until the patient is asleep. Once the patient is asleep, the method proceeds to monitoring whether the user is in a prone position (step 404) and whether the user is having a seizure (step 406). If the user is in the prone position (as determined at step 404), the system 10 repositions the user to the recovery position (step 408), then determines whether the user's biomarkers are normal (step 410). If the biomarkers are normal, then the method reverts back to step 402. If the biomarkers are abnormal, the system 10 stimulates the patient at step 412 and sends one or more alerts (step 414).

Turning back to step 406, if the system 10 determines that the user is having a seizure, the system 10 monitors the event (step 416) and determines whether the user is in the prone position (step 418). The system 10 then determines if the seizure is over (step 420). If not, then the system waits until the seizure is over (step 422). When the seizure is over, the system 10 reverts to step 408 to reposition the user to the recovery position and step 412 to stimulate the user, and then proceeds from steps 410 and 414 as described above.

With respect to simulation, the mattress 12 can accomplish stimulation by moving the user, shaking the user, or providing vibrations by adjusting a speed of inflation/deflation of the cells. For example, movement is described above, that is, by moving individual cells up or down to roll the user to a different position. Shaking and vibration can be accomplished by generating different speeds of inflation/deflation of the individual cells 18. For example, by opening and closing valves at different speeds, it may be possible to generate different "vibration frequencies" and vary such frequencies in order to stimulate a user.

While the above methods and processes are shown and described herein with steps in a particular order, it should be noted that, in some applications, certain steps or process blocks may be eliminated, added, or rearranged. For example, in any of the above methods, a practitioner or user can override certain process steps, for example, to manually adjust the mattress 12. As another example, in the method of FIG. 22, the initial step of determining whether the patient is asleep may be eliminated in order to monitor the user at any time while lying on the mattress 12 (i.e., while asleep or awake). Such a process may be beneficial for example, for high risk epilepsy patients in order to provide effective monitoring and fast intervention without human assistance.

Accordingly, in one particular application, the systems and methods can autonomously deliver intervention to prevent SUDEP. More specifically, there are currently no products that detect the prone position or have the ability to physically reposition a patient into a recovery position. The present systems and methods, on the other hand, can address the current unmet needs by providing a body repositioning device for patients with epilepsy that will autonomously perform the critical interventions of nocturnal supervision: repositioning and stimulating the patient after a convulsive seizure. By modeling body position continuously during sleep, the system can deliver information in greater detail regarding the relationship between nocturnal seizures and body positioning, thus providing greater efficacy than existing solutions. In particular, this type of information is impossible to ascertain from wearable devices alone and difficult to analyze from videos. The present system, on the other hand, can obtain this information from the matrix of embedded sensors in the bio-sensory cells that comprise the smart mattress. Furthermore, the expandable cells of the system represent a new structural concept to build mattresses and opens the possibility to implement dynamic robotic systems to the domestic sleeping health environment.

Additionally, the patient monitoring system can be used as a data collection device to help improve understanding of nocturnal seizures through autonomous data collection and analysis. Current outpatient data collection for nocturnal seizures requires wearable sensors, which are limited for long term data analysis due to inevitable decrease in patient compliance. A mattress not requiring any additional sensors to be worn does not require patient compliance. In addition, by continuously monitoring and modeling body positioning, this system will allow for a more comprehensive collection and analysis of nocturnal seizures. As it is likely that a seizure, even convulsive ones, will be difficult to generalize between patients but predictable within patient, this device will allow for personalized intervention after a period of use.

In light of the above, systems and methods of the present disclosure may be configured to perform one or more of the following functions: prevent prone positions in sleeping users without human supervision; reposition patients having a seizure into the recovery position without human supervision; monitor sleep patterns to recognize emergency events by tracking sleep patterns such as breathing, heart rate, muscular activity, temperature, and position patterns; stimulate and alert the user, other people, and/or emergency services when the sleeping user is at risk; assist mobility of users in bed; adjust bed conditions for better sleeping experience, and/or other functions.

While the present system and methods are described above with respect to seizure assistance and SUDEP prevention, it should be noted that the system and methods can be applied to other patient monitoring and positioning applications. For example, the present systems and methods can be used for preventing SIDS, managing wound pressure, in the ICU environment, to generally aid mobility in bed, obstructive sleep apnea (OSA) management, to help shoulder, back, or hip pain, for research purposes, precision medicine, non-medical uses, chiropractic applications, personalized medicine, bed mobility aids, as a sleep aid (e.g., to assist with pressure redistribution), among other applications.

The present invention has been described in terms of one or more preferred embodiments, and it should be appreciated that many equivalents, alternatives, variations, and modifications, aside from those expressly stated, are possible and within the scope of the invention. Furthermore, the term "about" as used herein means a range of plus or minus 20% with respect to the specified value, more preferably plus or minus 10%, even more preferably plus or minus 5%, most preferably plus or minus 2%. In the alternative, as known in the art, the term "about" indicates a deviation, from the specified value, that is equal to half of a minimum increment of a measure available during the process of measurement of such value with a given measurement tool.

The invention claimed is:

1. A system for patient monitoring and repositioning, the system comprising:

a mattress including:

a cell array with a plurality of individually height-adjustable cells each having sensor surface configured to sense at least one biomarker of the patient while lying on the mattress, and a base board array to receive the cell array and including a plurality of base boards, wherein at least one base board of the plurality of baseboards comprises a port interface having a plurality of ports and configured to be coupled to a connection manifold of a cell of the plurality of cells to physically, electronically, and pneumatically connect the cell to the at least one base board, and wherein the port interface is further configured to orient the cell on the at least one base board; and a main unit in communication with each cell of the cell array through the base board array, the main unit configured to receive data from each of the cells, including measurements of the at least one biomarker, and independently control a height of each of the cells.

2. The system of claim 1, wherein each of the cells includes:

a cushion portion;

a spring portion below the cushion portion; and a platform portion below the spring portion.

3. The system of claim 2, wherein the spring portion includes a pneumatically powered, expandable spring controlled by the main unit.

4. The system of claim 3, wherein the cushion portion includes the sensor surface, and the sensor surface comprises a sensor module with an array of sensors.

5. The system of claim 4, wherein the array of sensors includes at least one of a pressure sensor, an accelerometer, a sound sensor, a temperature sensor, and a humidity sensor.

6. The system of claim 3, wherein the main unit is configured to control expansion of the spring via an air source.

7. The system of claim 1, wherein the main unit is in communication with a wearable device, is configured to receive data about the patient from the wearable device, and is configured to independently control a height of each of the cells based on the data from the sensor surface and the data from the wearable device.

8. The system of claim 1 and further comprising a frame configured to support the mattress.

9. The system of claim 1, wherein the mattress further comprises a mattress pad and a mattress skirt configured to close around the cell array and the base board array.

10. The system of claim 1, wherein the main unit is configured to communicate data and alerts to at least one of a phone and an external computer.

11. A smart cell for use in a smart cell array that forms a smart mattress, the smart cell comprises:

a cushion layer comprising a cushion cover over a sensor module, the sensor module configured to sense at least one biomarker associated with a user lying on the cushion layer;

a spring layer comprising an expandable spring configured to adjust an overall height of the smart cell;

a platform layer configured to support the spring layer and the cushion layer and house a terminal board, the terminal board configured to control the expandable spring to adjust the overall height of the smart cell; and a connection manifold configured to physically, electronically, and pneumatically connect the smart cell to a port interface including a plurality of ports of a base board.

12. The smart cell of claim 11, wherein the cushion layer further comprises one or more foam layers under the sensor module, and a pad holder configured to hold the one or more foam layers, the sensor module, and the cushion cover.

13. The smart cell of claim 11, wherein the cushion layer is cuboid in shape.

14. The smart cell of claim 11, wherein the expandable spring is pneumatically powered, and the platform layer comprises at least one valve controlled by the terminal board to adjust an air volume within the expandable spring.

15. The smart cell of claim 11, wherein the sensor module includes an array of sensors within a sensor pocket, and the array of sensors includes at least one of a pressure sensor, an accelerometer, a sound sensor, a temperature sensor, and a humidity sensor.

16. A method for monitoring and repositioning a patient using a smart mattress system, the method comprising:

scanning the patient on the smart mattress system using a smart cell array including individual cells each having an independent sensing surface;

identifying a position of the patient on the smart mattress based on the scanning;

determining when the patient's position is a prone position; and automatically adjusting heights of one or more of the individual cells to reposition the patient out of the prone position;

wherein the smart mattress system includes:

a mattress including:

at least one base board including a port interface having a plurality of ports and configured to be coupled to a connection manifold of a cell of the individual cells to physically, electronically, and pneumatically connect the cell to the at least one base board, and wherein the port interface is further configured to orient the cell on the at least one base board.

17. The method of claim 16, further comprising determining when the patient is having a seizure; and waiting until the seizure is over to reposition the patient out of the prone position.

18. The method of claim 16 and further comprising monitoring at least one biomarker of the patient using the smart cell array.

19. The method of claim 16 and further comprising stimulating the patient after repositioning the patient out of the prone position.

* * * * *